United States Patent [19]

Kratt et al.

[11] Patent Number: 5,162,327
[45] Date of Patent: Nov. 10, 1992

[54] PYRIMIDINETRIONE DERIVATIVES, AGENTS CONTAINING THEM AND THEIR USE AS AGENTS FOR COMBATING PESTS

[75] Inventors: Günter Kratt, Eppstein; Gerhard Salbeck, Kriftel; Werner Bonin, Kelkheim; Dieter Düwel, Hofheim am Taunus, all of Fed. Rep. of Germany

[73] Assignee: Hoechst Aktiengesellschaft, Frankfurt am Main, Fed. Rep. of Germany

[21] Appl. No.: 474,379

[22] Filed: Feb. 2, 1990

[30] Foreign Application Priority Data

Feb. 6, 1989 [DE] Fed. Rep. of Germany ....... 3903404

[51] Int. Cl.$^5$ .................. A61K 31/515; C07D 239/62
[52] U.S. Cl. ..................................... 514/270; 514/272; 514/274; 544/296; 544/300; 544/301; 544/310; 544/311; 544/320; 544/321
[58] Field of Search ............... 544/301, 311, 313, 314, 544/320, 321; 514/270, 272, 274

[56] References Cited

U.S. PATENT DOCUMENTS 4,595,687 6/1986 Beight et al. ................... 544/311
4,808,587 2/1989 Go et al. ........................ 544/311

FOREIGN PATENT DOCUMENTS

| 18419/83 | 3/1984 | Australia . |
| 18420/83 | 3/1984 | Australia . |
| 535847 | 3/1955 | Belgium . |
| 0004400 | 10/1979 | European Pat. Off. . |
| 0102327 | 3/1984 | European Pat. Off. . |
| 0105030 | 4/1984 | European Pat. Off. . |
| 0167491 | 1/1986 | European Pat. Off. . |
| 1185302 | 7/1959 | France . |
| 2370746 | 6/1978 | France . |

Primary Examiner—C. Warren Ivy
Assistant Examiner—James H. Turnipseed
Attorney, Agent, or Firm—Curtis, Morris & Safford

[57] ABSTRACT

Pyrimidinetrione derivatives, processes for their preparation, agents containing them and their use as agents for combating pests.

Compounds of the formula I, tautomeric forms thereof of the formula Ia, stereoisomers thereof and the mixtures of these forms wherein $R^1$ and $R^2$ denote unsubstituted or substituted alkyl, alkenyl, alkynyl; alkoxy, alkylsulfonyl, alkylcarbonyl or cyano or optionally substituted phenyl, phenylsulfonyl or phenylcarbonyl, $R^3$ denotes hydrogen, alkyl or optionally substituted phenyl, $R^4$ denote H, OH, unsubstituted or substituted alkyl, alkenyl, alkynyl, phenylsulfonyl, phenylcarbonyl, phenylcarbamoyl or phenyl; alkylsulfonyl or alkylcarbonyl, which can be halogenated, alkylcarbamoyl or cyano, $R^5$ and $R^6$ denote halogen, alkoxy, alkylcarbonyl, alkoxycarbonyl, alkylsulfenyl, -sulfinyl or -sulfonyl, haloalkoxy, alkylamino, cyano, sulfo or nitro, A,X,Z and L denote oxygen, sulfur, sulfinyl, sulfonyl or nitrogen, which can be substituted by alkyl, or L denotes a double bond, M,D,E,Q and G denote carbon or nitrogen, V denotes carbon or substituted phosphorus, W denotes alkylene or haloalkylene, both of which can be substituted, $Y^1$ denotes H, halogen, alkyl, alkylamino or hydroxyl, $Y^2$ denotes oxygen, sulfur or nitrogen which is optionally substituted by alkyl and n amd m denote 0-4, and salts thereof which can be employed in agriculture or are physiologically tolerated, have advantageous actions against a broad spectrum or animal pests in agriculture and animal breeding.

9 Claims, No Drawings

PYRIMIDINETRIONE DERIVATIVES, AGENTS CONTAINING THEM AND THEIR USE AS AGENTS FOR COMBATING PESTS

DESCRIPTION

Barbituric acid derivatives having an insecticidal or anthelmintic activity are known from EP-A 102,327. However, these compounds in some cases have inadequate activities.

Novel substituted pyrimidinetriones have been found, which are distinguished by advantageous properties in combating pests, such as, for example, harmful insects or endoparasites.

The present invention thus relates to the compounds of the formula I, tautomeric forms thereof of the formula Ia, stereoisomers thereof and the mixtures of these forms

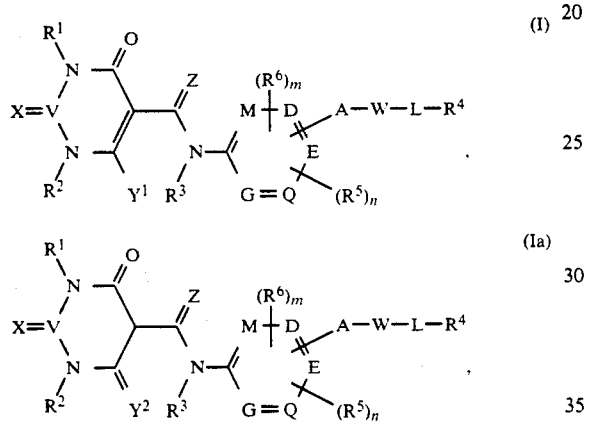

wherein
$R^1$ and $R^2$ independently of one another denote $(C_1-C_6)$-alkyl, $(C_2-C_6)$-alkenyl or $(C_2-C_6)$-alkynyl, all of which can be substituted by one to thirteen halogen atoms and/or mono-, di- or trisubstituted by a radical from the group comprising $(C_1-C_4)$-alkoxy, $(C_1-C_4)$-alkoxycarbonyl, $(C_2-C_4)$-alkylsulfenyl, $(C_1-C_4)$-alkylsulfinyl, $(C_1-C_4)$-alkylsulfonyl, di$(C_1-C_4)$-alkylamino, cyano, sulfo, nitro, hydroxyl, carboxyl, phenyl or phenoxy, it being possible for the last two radicals mentioned to be mono-, di- or trisubstituted by a radical from the group comprising halogen, $(C_1-C_4)$-alkyl, $(C_1-C_4)$-alkoxy, $(C_1-C_4)$-alkylcarbonyl, $(C_1-C_4)$-alkoxycarbonyl, $(C_1-C_4)$-alkylsulfenyl, $(C_1-C_4)$-alkylsulfinyl, $(C_1-C_4)$-alkylsulfonyl, halo$(C_1-C_4)$-alkoxy having in the last case one to nine halogen atoms; di$(C_1-C_4)$alkylamino, cyano, sulfo and nitro; $(C_1-C_4)$-alkoxy, $(C_1-C_4)$-alkylsulfonyl, $(C_1-C_4)$-alkylcarbonyl, cyano, phenylsulfonyl or phenylcarbonyl, it being possible for the last two radicals mentioned to be substituted by one to three radicals from the group comprising halogen, $(C_1-C_4)$-alkyl, $(C_1-C_4)$-alkoxy, halo$(C_1-C_4)$-alkoxy having in the last case one to nine halogen atoms; and nitro; phenyl which can be substituted by one to three radicals from the group comprising halogen, $(C_1-C_4)$-alkyl, $(C_1-C_4)$-alkoxy, $(C_1-C_4)$-alkylcarbonyl, $(C_1-C_4)$-alkoxycarbonyl, $(C_1-C_4)$-alkylsulfenyl, $(C_1-C_4)$-alkylsulfinyl, $(C_1-C_4)$-alkylsulfonyl, halo$(C_1-C_4)$-alkyl, halo$(C_1-C_4)$-alkoxy having in the last two cases one to nine halogen atoms di$(C_1-C_4)$-alkylamino, cyano, sulfo, nitro and phenoxy, which is optionally substituted by one to three radicals from the group comprising halogen, $(C_1-C_4)$-alkyl and $(C_1-C_4)$-alkoxy, $R^3$ denotes hydrogen or $(C_1-C_6)$-alkyl; or phenyl, which can be substituted by one to three radicals from the group comprising halogen, $(C_1-C_4)$-alkyl, $(C_1-C_4)$-alkoxy, $(C_1-C_4)$-alkylcarbonyl, $(C_1-C_4)$-alkoxycarbonyl, $(C_1-C_4)$-alkylsulfenyl, $(C_1-C_4)$-alkylsulfinyl, $(C_1-C_4)$-alkylsulfonyl, halo$(C_1-C_4)$-alkyl, halo$(C_1-C_4)$-alkoxy having in the last two cases one to nine halogen atoms; di$(C_1-C_4)$-alkylamino, cyano, sulfo, nitro and phenoxy, which is optionally substituted by one to three radicals from the group comprising halogen, $(C_1-C_4)$-alkyl and $(C_1-C_4)$-alkoxy, $R^4$ denotes hydrogen, $(C_1-C_6)$-alkyl, $(C_2-C_6)$-alkenyl or $(C_2-C_6)$-alkynyl, all of which can be substituted by one to nine halogen atoms and/or mono-, di- or trisubstituted by a radical from the group comprising $(C_1-C_6)$-alkoxy, halo$(C_1-C_6)$-alkoxy, $(C_1-C_6)$-alkoxycarbonyl, halo$(C_1-C_6)$-alkoxycarbonyl, $(C_1-C_6)$-alkylsulfenyl, $(C_1-C_6)$-alkylsulfinyl, $(C_1-C_6)$-alkylsulfonyl, di$(C_1-C_6)$-alkylamino, cyano, sulfo, nitro, hydroxyl, carboxyl, phenyl and phenoxy, it being possible for the last two radicals mentioned to be mono-, di- or trisubstituted by a radical from the group comprising halogen, $(C_1-C_4)$-alkyl, halo$(C_1-C_4)$-alkyl having in the last case one to nine halogen atoms, $(C_1-C_4)$-alkoxy, $(C_1-C_4)$-alkylcarbonyl, halo$(C_1-C_4)$-alkylcarbonyl, $(C_1-C_4)$-alkoxycarbonyl, halo$(C_1-C_4)$-alkoxycarbonyl, $(C_1-C_4)$alkylsulfenyl, $(C_1-C_4)$-alkylsulfinyl, $(C_1-C_4)$-alkylsulfonyl, sulfato, halo$(C_1-C_4)$-alkoxy having in last case one to nine halogen atoms; di$(C_1-C_4)$-alkylamino, cyano, sulfo and nitro; $(C_1-C_6)$-alkylsulfonyl, $(C_1-C_6)$-alkylcarbonyl, halo$(C_1-C_6)$-alkylsulfonyl, halo$(C_1-C_6)$-alkylcarbonyl, mono- or di$(C_1-C_4)$-alkylcarbamoyl, cyano, phenylsulfonyl, phenylcarbonyl or phenylcarbamoyl, it being possible for the last three radicals mentioned to be substituted by one to three radicals from the group comprising halogen, $(C_1-C_4)$-alkyl, halo$(C_1-C_4)$-alkyl, $(C_1-C_4)$-alkoxy, halo$(C_1-C_4)$-alkoxy, $(C_1-C_4)$-alkylcarbonyl, halo$(C_1-C_4)$-alkylcarbonyl, $(C_1-C_4)$-alkoxycarbonyl, halo$(C_1-C_4)$-alkoxycarbonyl, $(C_1-C_4)$-alkylsulfenyl, $(C_1-C_4)$-alkylsulfinyl, $(C_1-C_4)$-alkylsulfonyl, di$(C_1-C_4)$-alkylamino, cyano, sulfo and nitro; or phenyl, which can be substituted by one to three radicals from the group comprising halogen, $(C_1-C_4)$-alkyl, $(C_1-C_4)$-alkoxy, $(C_1-C_4)$-alkylcarbonyl, $(C_1-C_4)$-alkoxycarbonyl, $(C_1-C_4)$-alkylsulfenyl, $(C_1-C_4)$-alkylsulfinyl, $(C_1-C_4)$-alkylsulfonyl, halo$(C_1-C_4)$-alkyl, halo$(C_1-C_4)$-alkoxy having in last two cases one to nine halogen atoms; di$(C_1-C_4)$-alkylamino, cyano, sulfo, nitro and phenoxy, which is optionally substituted by one to three radicals from the group comprising halogen, $(C_1-C_4)$-alkyl and $(C_1-C_4)$-alkoxy, $R^5$ and $R^6$ independently of one another denote halogen, $(C_1-C_4)$-alkyl, $(C_1-C_4)$-alkoxy, $(C_1-C_4)$-alkylcarbonyl, $(C_1-C_4)$-alkoxycarbonyl, $(C_1-C_4)$-alkylsulfenyl, $(C_1-C_4)$-alkylsulfinyl, $(C_1-C_4)$-alkylsulfonyl, halo$(C_1-C_4)$-alkyl, halo$(C_1-C_4)$-alkoxy having in the last two cases one to nine halogen atoms; di$(C_1-C_4)$-alkylamino, cyano, sulfo or nitro, A, X and Z independently of one another denote oxygen, sulfur, sulfinyl, sulfonyl or nitrogen, which can be substituted by $(C_1-C_4)$-alkyl, L denotes oxygen, sulfur, sulfinyl, sulfonyl or nitrogen, which can be substituted by $(C_1-C_4)$-alkyl; or a double bond, M,D,E,Q and G independently of one another denote carbon or nitrogen, V denotes carbon or phosphorus, which is substituted by $(C_1-C_6)$-alkoxy, $(C_1-C_4)$-alkylthio, phenoxy or phenylthio, both of which can carry one to three radicals from the group comprising halogen, $(C_1-C_4)$-alkyl, $(C_1-C_4)$-alkoxy, $(C_1-C_4)$-alkylcarbonyl, $(C_1-C_4)$-alkoxycarbonyl, $(C_1-C_4)$-alkylsulfenyl, $(C_1-C_4)$-alkylsulfinyl, $(C_1-C_4)$-alkylsulfonyl, halo$(C_1-C_4)$-alkyl, halo$(C_1-C_4)$-alkoxy having in the last two cases one to nine halogen atoms, di$(C_1-C_4)$-alkylamino; cyano, sulfo and nitro, W denotes $(C_1-C_{10})$-alkylene or halo$(C_1-C_{10})$-alkylene, which can be substituted by one to five radicals from the group comprising $(C_1-C_4)$-alkyl, halo$(C_1-C_4)$-alkyl, $(C_1-C_4)$-alkoxy, halo$(C_1-C_4)$-alkoxy, cyano or nitro, $Y^1$ denotes H, halogen, $(C_1-C_4)$-alkyl, amino, $(C_1-C_4)$-alkylamino, di$(C_1-C_4)$-alkylamino or hydroxyl, $Y^2$ denotes oxygen, sulfur or nitrogen, which can be substituted by $(C_1-C_4)$-alkyl, and n and m independently of one another denote the numbers 0 to 4, and salts thereof which can be employed in agriculture or are physiologically tolerated.

In these definitions, alkyl denotes straight-chain or branched alkyl and alkylene denotes an unsaturated hydrocarbon radical which can contain one or more double bonds.

Preferred compounds of the formulae I and Ia are those in which $R^1$ and $R^2$ independently of one another denote $(C_1-C_6)$-alkyl, $(C_2-C_6)$-alkenyl or $(C_2-C_6)$-alkynyl, which can be substituted by one to thirteen halogen atoms and/or mono-, di- or trisubstituted by a radical from the group comprising $(C_1-C_4)$-alkoxy, $(C_1-C_4)$-alkoxycarbonyl, $(C_1-C_4)$-alkylsulfenyl, di$(C_1-C_4)$-alkylamino, cyano, sulfo, nitro, hydroxyl, carboxyl, phenyl or phenoxy, it being possible for the last two radicals mentioned to be mono-, di- or trisubstituted by a radical from the group comprising halogen, $(C_1-C_4)$-alkyl, $(C_1-C_4)$-alkoxy, $(C_1-C_4)$-alkylcarbonyl, $(C_1-C_4)$-alkoxycarbonyl, $(C_1-C_4)$-alkylsulfenyl, $(C_1-C_4)$-alkylsulfinyl, $(C_1-C_4)$-alkylsulfonyl, halo-$(C_1-C_4)$-alkoxy having in last case one to nine halogen atoms; di$(C_1-C_4)$-alkylamino, cyano, sulfo and nitro, $R^3$ denotes hydrogen or $(C_1-C_6)$-alkyl, $R^4$ denotes hydrogen, $(C_1-C_6)$-alkyl, $(C_2-C_6)$-alkenyl or $(C_2-C_6)$-alkynyl, all of which can be substituted by one to nine halogen atoms and/or mono-, di- or trisubstituted by a radical from the group comprising $(C_1-C_6)$-alkoxy, halo$(C_1-C_6)$-alkoxy, $(C_1-C_6)$-alkoxycarbonyl, halo$(C_1-C_6)$-alkoxycarbonyl, $(C_1-C_6)$-alkylsulfenyl, cyano, sulfo, nitro, hydroxyl, carboxyl, phenyl and phenoxy, it being possible for the last three radicals mentioned to be mono-, di- or trisubstituted by a radical from the group comprising halogen, $(C_1-C_4)$-alkyl, halo$(C_1-C_4)$-alkyl, $(C_1-C_4)$-alkoxy, halo$(C_1-C_4)$-alkoxy, $(C_1-C_4)$-alkylcarbonyl, halo$(C_1-C_4)$-alkylcarbonyl, $(C_1-C_4)$-alkoxycarbonyl, halo$(C_1-C_4)$-alkoxycarbonyl, $(C_1-C_4)$-alkylsulfenyl, $(C_1-C_4)$-alkylsulfinyl, $(C_1-C_4)$-alkylsulfonyl, di$(C_1-C_4)$-alkylamino, cyano, sulfo and nitro; $(C_1-C_6)$-alkylsulfonyl, $(C_1-C_6)$-alkylcarbonyl, halo$(C_1-C_6)$-alkylsulfonyl, halo$(C_1-C_6)$-alkylcarbonyl, mono-, di$(C_1-C_4)$-alkylcarbamoyl, cyano, phenylsulfonyl, phenylcarbonyl or phenylcarbamoyl, it being possible for the last three radicals mentioned to be substituted by one to three radicals from the group comprising halogen, $(C_1-C_4)$-alkyl, halo$(C_1-C_4)$-alkyl, $(C_1-C_4)$-alkoxy, halo$(C_1-C_4)$-alkoxy, $(C_1-C_4)$-alkylcarbonyl, halo$(C_1-C_4)$-alkylcarbonyl, $(C_1-C_4)$-alkoxycarbonyl, halo$(C_1-C_4)$-alkoxycarbonyl, $(C_1-C_4)$-alkylsulfenyl, $(C_1-C_4)$-alkylsulfinyl, $(C_1-C_4)$-alkylsulfonyl, di$(C_1-C_4)$-alkylamino, cyano, sulfo and nitro, $R^5$ and $R^6$ independently of one another denote halogen, $(C_1-C_4)$-alkyl, $(C_1-C_4)$-alkoxy, $(C_1-C_4)$-alkylcarbonyl, $(C_1-C_4)$-alkoxycarbonyl, $(C_1-C_4)$-alkylsulfenyl, halo$(C_1-C_4)$-alkoxy having in the last case one to nine halogen atoms; di$(C_1-C_4)$-alkylamino, cyano, sulfo and nitro, A, X and Z independently of one another denote oxygen, sulfur, sulfinyl or sulfonyl, L denotes oxygen, sulfur, sulfinyl, sulfonyl or nitrogen, which can be substituted by $(C_1-C_4)$-alkyl; or a double bond, M,D,E,Q and G independently of one another denote carbon or nitrogen, V denotes carbon or phosphorus, which is substituted by $(C_1-C_6)$-alkoxy, $(C_1-C_4)$-alkylthio, phenoxy or phenylthio, both of which can carry one to three radicals from the group comprising halogen, $(C_1-C_4)$-alkyl, $(C_1-C_4)$-alkoxy, halo$(C_1-C_4)$-alkoxy, cyano, sulfo and nitro, W denotes $(C_1-C_{10})$-alkylene or halo$(C_1-C_{10})$-alkylene, which can be substituted by one to five radicals from the group comprising $(C_1-C_4)$-alkyl, halo$(C_1-C_4)$-alkyl, $(C_1-C_4)$-alkoxy, halo$(C_1-C_4)$-alkoxy, cyano and nitro, $Y^1$ denotes H, halogen, $(C_1-C_4)$-alkyl, amino, $(C_1-C_4)$-alkylamino, di$(C_1-C_4)$-alkylamino or hydroxyl, $Y^2$ denotes oxygen, sulfur or nitrogen, which can be substituted by $(C_1-C_4)$-alkyl, and n and m independently of one another denote the numbers 0 to 4, and salts thereof which can be employed in agriculture or are physiologically tolerated.

Particularly preferred compounds of the formulae I and Ia are those in which $R^1$ and $R^2$ independently of one another denote $(C_1-C_6)$-alkyl, $(C_2-C_6)$-alkenyl or $(C_2-C_6)$-alkynyl, which can be substituted by one to thirteen halogen atoms and/or $(C_1-C_4)$-alkoxy, $(C_1-C_4)$-alkoxycarbonyl or $(C_1-C_4)$-alkylsulfenyl, $R^3$ denotes hydrogen or $(C_1-C_6)$-alkyl, $R^4$ denotes hydrogen, $(C_1-C_6)$-alkyl, $(C_2-C_6)$-alkenyl or $(C_2-C_6)$-alkynyl, all of which can be substituted by one to nine halogen atoms and/or mono-, di- or trisubstituted by a radical from the group comprising $(C_1-C_6)$-alkoxy, halo$(C_1-C_6)$-alkoxy, $(C_1-C_6)$-alkoxycarbonyl, halo$(C_1-C_6)$-alkoxycarbonyl, $(C_1-C_6)$-alkylsulfenyl, $(C_1-C_6)$-alkylsulfinyl, di$(C_1-C_6)$-alkylamino, cyano, sulfo, nitro, hydroxyl and carboxyl; or $(C_1-C_6)$-alkylsulfonyl, $(C_1-C_6)$-alkylcarbonyl, halo$(C_1-C_6)$-alkylsulfonyl, halo$(C_1-C_6)$- alkylcarbonyl or mono- or di($C_1$-$C_4$)-alkylcarbamoyl, $R^5$ and $R^6$ independently of one another denote halogen, ($C_1$-$C_4$)-alkyl, ($C_1$-$C_4$)-alkoxy, ($C_1$-$C_4$)-alkylcarbonyl, ($C_1$-$C_4$)-alkoxycarbonyl, ($C_1$-$C_4$)-alkylsulfenyl, halo($C_1$-$C_4$)-alkoxy having in the last case one to nine halogen atoms; di($C_1$-$C_4$)-alkylamino, cyano, sulfo or nitro, A, X and Z independently of one another denote oxygen or sulfur, L denotes oxygen, sulfur or nitrogen, which can be substituted by ($C_1$-$C_4$)-alkyl; or a double bond, M,D,E,Q and G independently of one another denote carbon or nitrogen, V denotes carbon, W denotes ($C_1$-$C_{10}$)-alkylene or halo($C_1$-$C_{10}$)-alkylene, which can be substituted by one to five radicals from the group comprising ($C_1$-$C_4$)-alkyl, halo($C_1$-$C_4$)-alkyl, ($C_1$-$C_4$)-alkoxy or halo($C_1$-$C_4$)-alkoxy, $Y^1$ denotes H, amino or hydroxyl, $Y^2$ denotes oxygen, sulfur or nitrogen, which can be substituted by ($C_1$-$C_4$)-alkyl, and n and m independently of one another denote the numbers 0 to 4, and salts thereof which can be employed in agriculture or are physiologically tolerated.

The substituent chain —A—W—L—$R^4$ is preferably in the 2-, 3- or 4-position on the phenyl nucleus or on the N-containing heterocyclic radical. Depending on the position of this substituent chain, the remaining ring substituents $R^5$ and $R^6$ have, in particular, the following meanings (substitution pattern):

for 4-AWLR$^4$:
$R^5$: hydrogen, 2-halogeno, 2-($C_1$-$C_6$)-alkyl, 2-carboxy, 2-($C_1$-$C_6$)-alkoxycarbonyl, 3-halogeno, 3-($C_1$-$C_6$)-alkyl, 3-carboxy or 3-($C_1$-$C_6$)-alkoxycarbonyl,
$R^6$: hydrogen or 5-halogeno;

for 3-AWLR$^4$:
$R^5$: hydrogen, 2-halogeno, 2-($C_1$-$C_6$)-alkyl, 2-carboxy or 2-($C_1$-$C_6$)-alkoxycarbonyl,
$R^6$: hydrogen, 4-halogeno, 5-halogeno or 6-halogeno
or
$R^5$: 4-halogeno, 4-($C_1$-$C_6$)-alkyl, 4-carboxy or 4-($C_1$-$C_6$)-alkoxycarbonyl,
$R^6$: hydrogen, 2-halogeno, 5-halogeno or 6-halogeno
or
$R^5$: 5-halogeno, 5-($C_1$-$C_6$)-alkyl, 5-carboxy or 5-($C_1$-$C_6$)-alkoxycarbonyl,
$R^6$: hydrogen, 2-halogeno, 4-halogeno or 6-halogeno
or
$R^5$: 6-halogeno, 6-($C_1$-$C_6$)-alkyl, 6-carboxy or 6-($C_1$-$C_6$)-alkoxycarbonyl,
$R^6$: hydrogen, 2-halogeno, 4-halogeno or 5-halogeno;

for 2-AWLR$^4$:
$R^5$: hydrogen, 3-halogeno, 3-($C_1$-$C_6$)-alkyl, 3-carboxy or 3-($C_1$-$C_6$)-alkoxycarbonyl,
$R^6$: hydrogen, 4-halogeno, 5-halogeno or 6-halogeno
or
$R^5$: 4-halogeno, 4-($C_1$-$C_6$)-alkyl, 4-carboxy or 4-($C_1$-$C_6$)-alkoxycarbonyl,
$R^6$: hydrogen, 3-halogeno, 5-halogeno or 6-halogeno
or
$R^5$: 5-halogeno, 5-($C_1$-$C_6$)-alkyl, 5-carboxy or 5-($C_1$-$C_6$)-alkoxycarbonyl,
$R^6$: hydrogen, 3-halogeno, 4-halogeno or 6-halogeno
or
$R^5$: 6-halogeno, 6-($C_1$-$C_6$)-alkyl, 6-carboxy or 6-($C_1$-$C_6$)-alkoxycarbonyl,
$R^6$: hydrogen, 3-halogeno, 4-halogeno or 5-halogeno.

The invention also relates to all the stereoisomers and mixtures thereof of the compounds of the formulae (I) and (Ia), such as the E- and Z-isomers in the case of unsaturated structures or the optical isomers if chirality centers occur.

Possible salts of the compounds of the formulae I and Ia are, in particular, the alkali metal, alkaline earth metal or ammonium salts or ammonium salts which are substituted by one to four organic radicals (such as alkyl or hydroxyalkyl).

In the case where $R^4$ and/or $Y^1$=OH in particular, the salts are formed by deprotonation of the oxygen with the corresponding bases.

Bases which are preferably used for the salt formation are the hydroxides, alcoholates, hydrides or metal alkyls or aryls of the alkali or alkaline earth metals, such as, for example, sodium hydroxide or potassium hydroxide, sodium methylate or ethylate or potassium tert.-butylate, sodium hydride, potassium hydride or calcium hydride, methyl-, n-butyl-, tert.-butyl- or phenyllithium or ammonia or primary, secondary or tertiary amines, such as methylamine, diethylamine or triethylamine. The actual reaction is carried out by methods which are known to the expert.

The present invention also relates to processes for the preparation of the compounds (I) and (Ia), which comprise a) reacting a compound of the formula (II) or (III)

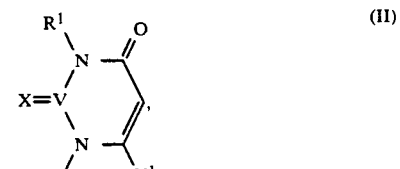

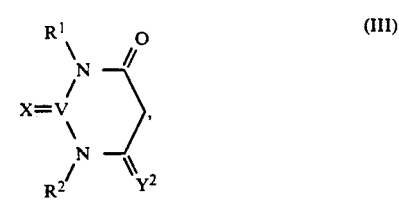

in which $R^1$, $R^2$, V, X, $Y^1$ and $Y^2$ have the same meaning as in the formulae (I) and (Ia), with a compound of the formula (IV)

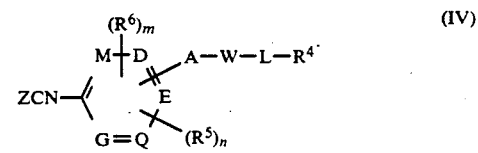

in which A, L, M, D, E, Q, G, W, Z, $R^4$, $R^5$, $R^6$, n and m have the same meaning as in formulae (I) and (Ia), or b) reacting a compound of the formula (V) or (VI)

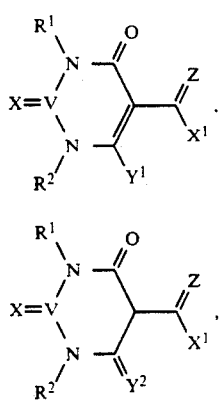

in which $R^1$, $R^2$, V, X, $Y^1$, $Y^2$ and Z have the same meaning as in the formulae (I) and (Ia) and $X^1$ represents a nucleofugic leaving group, such as, for example, halogen, $(C_1-C_6)$-alkoxy, $(C_1-C_6)$-alkylthio, phenyl, imidazolyl or triazolyl, with a compound of the formula (VII)

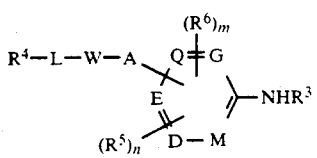

in which A, L, M, D, E, Q, G, W, $R^3$, $R^4$, $R^5$, $R^6$, n and m have the same meaning as in formulae (I) and (Ia).

The preparation of the pyrimidine derivatives of the formulae (II) and (III) (for example Y=Hal, $NH_2$ or OH, Beilstein E III/IV, Volume 25, pages 4108-4109 or Beilstein II, Volume 24, page 270) and of the pyrimidine-5-carboxylic acid derivatives (V) and (VI) (for example Y=OH, $NH_2$, OEt ester or OPh ester) are known from the literature (K. Bredereck, R. Richter, Chem. Ber. 98, 131 (1965) or J.-L. Bernier et al., Bull. Soc. Chim. France 1976, 616).

The compounds of the formula (IV) are obtained by methods which are known from the literature from the amines of the formula (VII) (Houben Weyl E4, page 738 and page 834).

The amines of the formula (VII) can be prepared by processes which are known from the literature, such as, for example, by reaction of the corresponding aminophenols with fluorinated olefins (for example U.S. Pat. No. 3,409,274) or by reduction of the corresponding nitro compounds (for example J. Soc. Dyers Col. 42, 78 (1926)).

The reactions for the preparation the compounds I and Ia are carried out in the presence of a solvent which is inert towards the participants of the reaction. Preferred possible solvents are aliphatic and aromatic hydrocarbons, such as cyclohexane, toluene or xylene, ethers, such as dioxane, glycol dimethyl ether or tetrahydrofuran, chlorinated hydrocarbons, such as methylene chloride, chloroform or carbon tetrachloride, nitriles, such as acetonitrile, or mixtures of such solvents.

The reactions for the preparation of the compounds I or Ia are carried out at temperatures between $-10°$ C. and the boiling point of the particular solvent used and over reaction times of 10 minutes to 12 hours. If $Y^1$=hydroxyl, temperatures of 50° C.-120° C. and reaction times of 1-4 hours are preferred, and if $Y^1$=amino or $(C_1-C_4)$-alkylamino, 80°-180° C. and 2-10 hours are preferred. The reactions for salt formation are preferably carried out at $-10-+70°$ C. over reaction times of 10 minutes-5 hours.

The compounds of the formulae IV and VII are novel and the present invention likewise relates to these compounds.

The active compounds have good plant tolerance and favorable toxicity towards warm-blooded animals and are suitable for combating animal pests, in particular insects, arachnida, helminths and mollusks, and especially preferably for combating insects and arachnida, encountered in agriculture, in animal breeding, in forestry, in the preservation of stored products and materials and in the hygiene sector. They are active against normally sensitive and resistant species and against all or some stages of development. The above-mentioned pests include:

From the order of the Acarina, for example, *Acarus siro*, Agras spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp., Eotetranychus spp., Oligonychus spp. and Eutetranychus spp.

From the order of the Isopoda, for example, *Oniscus aselus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blatella germanica, Acheta domesticus*, Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix*, Pemphigus spp., *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporarium, Aphis gossypii, Bravicornyne brassicae, Cryptomyzus ribis, Doralis fabae, Doralis pomi, Eriosoma lanigerum, Hyalopterus arundinis, Macrosiphium avenae*, Myzus spp., *Phorodon humuli, Rhopalosiphum padi*, Empoasca spp., *Euscelus bilobatus, Nephotettix cincticeps, Lecanium corni, Saissetia oleae, Laodelphax striatellus, Nilaparvata*

*lugens, Aonidiella auroantii, Apidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosma neustria, Euproctis chrysorrhoea,* Lymantria spp., *Bucculatrix thurberiella, Phyllocnistis citrella,* Agrotis spp., Euxoa spp., Feltia spp., Earias insulana, Heliothis spp., *Laphygma exigua, Mamestra brassicae, Panolis flammea, Prodenia litura,* Spodoptera spp., Trichoplusia ni, *Carpocapsa pomonella,* Pieris spp., Chilo spp., *Pyrausta nubilalis, Ephestia kuehniella, Galleria mellonella, Cocoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylloides chrysocephala, Epilachna varivestis,* Atomaria spp., *Oryzaephilus surinamensis,* Anthonumus spp., Sitophilus spp., *Otiorrhynchus sulcatus, Cosmopolites sordidus, Ceuthorrhynchus assimilis, Hypera postica,* Dermestes spp., Trogoderma, Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tripula paludosa.*

From the order of the Siphonaptera, for example, *Xenopsylla cheopsis* and Ceratophyllus spp.

From the order of the Arachnida, for example, *Scorpio maurus* and *Latrodectus mactans.*

From the class of Helminths, for example, Haemonchus, Trichostrongylus, Ostertagia, Cooperia, Chabertia, Strongyloides, Oesophagostomum, Hyostrongylus, Ancylostoma, Ascaris and Heterakis as well as Fasciola and phytopathogenic nematodes, for example those of the genera Meloidogyne, Heterodera, Ditylenchus, Aphelenchoides, Radopholus, Globodera, Pratylenchus, Longidorus and Xiphinema.

From the class of Gastropoda, for example, Deroceras spp., Arion spp., Lymnaea spp., Galba spp., Succinea spp., Biophalaria spp., Bulinus spp. and Oncomelania spp.

From the class of Bivalva, for example, Dreissena spp.

The present invention thus also relates to veterinary pharmaceuticals which contain or consist of an effective amount of a compound of the formulae I or Ia.

The invention also relates to agents which contain the compounds of the formula I, in addition to suitable formulation auxiliaries.

The agents according to the invention in general contain the active compounds of the formula I or Ia to the extent of 1 to 95% by weight.

They can be formulated in various ways, depending on the biological and/or chemico-physical parameters. Appropriate formulation possibilities are therefore: wettable powders (WP), emulsifiable concentrates (EC), aqueous solutions (SC), emulsions, sprayable solutions, oil- or water-based dispersions (SC), suspoemulsions (SC), dusting agents (DP), dressings, granules in the form of microgranules, sprayed granules, coated granules and adsorption granules, water-dispersible granules (WG), ULV formulations, microcapsules, waxes or baits.

These individual types of formulation are known in principle and are described, for example, in: Winnacker-Küchler, "Chemische Technologie (Chemical Technology)", Volume 7, C. Hauser Verlag Munich, 4th edition 1986; van Falkenberg, "Pesticides Formulations", Marcel Dekker N.Y., 2nd edition 1972–73; and K. Martens, "Spray Drying Handbook", 3rd edition 1979, G. Goodwin Ltd. London.

The formulation auxiliaries required, such as inert materials, surfactants, solvents and other additives, are likewise known and are described, for example, in: Watkins, "Handbook of Insecticide Dust Diluents and Carriers", 2nd edition, Darland Books, Caldwell N.J.; H. v. Olphen, "Introduction to Clay Colloid Chemistry", 2nd edition, J. Wiley & Sons, N.Y.; Marschen, "Solvents Guide", 2nd edition, Interscience, N.Y. 1950; McCutcheon's, "Detergents and Emulsifiers Annual", MC Publ. Corp., Ridgewood, N.J.; Sisley and Wood, "Encyclopedia of Surface Active Agents", Chem. Publ. Co. Inc., N.Y. 1964; Schönfeldt, "Grenzflächenaktive Äthylenoxidaddukte (Surface-active Ethylene Oxide Adducts)", Wiss. Verlagsgesell., Stuttgart 1976; Winnacker-Küchler, "Chemische Technologie (Chemical Technology)", Volume 7, C. Hauser Verlag Munich, 4th edition 1986.

Combinations with other pesticidally active substances, fertilizers and/or growth regulators can be prepared on the basis of these formulations, for example in the form of a finished formulation or as a tank mix.

Wettable powders are preparations which are uniformly dispersible in water and which also contain, alongside the active compound, and in addition to a diluent or inert substance, wetting agents, for example polyoxyethylated alkylphenols, polyoxyethylated fatty alcohols and alkyl- or alkylphenol-sulfonates, and dispersing agents, for example sodium ligninsulfonate, sodium 2,2'-dinaphthylmethane-6,6'-disulfonate, sodium dibutylnaphthalenesulfonate or sodium oleyl-methyltaurate. Emulsifiable concentrates are prepared by dissolving the active compound in an organic solvent, for example butanol, cyclohexanone, dimethylformamide, xylene or higher-boiling aromatics or hydrocarbons, with addition of one or more emulsifiers. Examples of emulsifiers which can be used are: calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxideethylene oxide condensation products, alkyl polyethers, sorbitan fatty acid esters, polyoxyethylene sorbitan fatty acid esters or polyoxyethylene sorbitol esters.

Dusting agents are obtained by grinding the active compound with finely divided solid substances, for example talc or naturally occurring clays, such as kaolin, bentonite, pyrophillite or diatomaceous earth. Granules can be prepared either by atomizing the active compound onto an absorbent granular inert material or by applying active compound concentrates to the surface of carriers, such as sand or kaolinites, or of granular inert material by means of adhesives, for example polyvinyl alcohol, sodium polyacrylate or mineral oils.

Suitable active compounds can also be granulated in the manner customary for the preparation of fertilizer granules—if desired as a mixture with fertilizers.

The active compound concentration in wettable powders is, for example, about 10 to 90% by weight, the remainder to make up 100% by weight consisting of the customary formulation constituents. The active compound concentration in emulsifiable concentrates can be about 5 to 80% by weight. Dust-like formulations usually contain 5 to 20% by weight of active compound, and sprayable solutions usually contain about 2 to 20% by weight. In granules, the active compound content depends partly on whether the active compound is in liquid or solid form and on what granulation auxiliaries, fillers and the like are used.

In addition, the active compound formulations mentioned contain, if appropriate, the particular customary adhesives, wetting agents, dispersing agents, emulsifiers, penetration agents, solvents, fillers or carriers.

For use, the concentrates in the commercially available form are diluted, if appropriate, in the customary manner, for example by means of water in the case of wettable powders, emulsifiable concentrates, dispersions and sometimes also microgranules. Dust-like and granular formulations and sprayable solutions are usually not additionally diluted with further inert substances before use.

The application amount required varies according to the external conditions, such as temperature, humidity and the like. It can vary within wide limits, for example between 0.005 and 10.0 kg/ha or more of active substance, but is preferably between 0.01 and 5 kg/ha.

The active compounds according to the invention can be present in their commercially available formulations and in the use forms prepared from these formulations as mixtures with other active compounds, such as insecticides, attractants, sterilizing agents, acaricides, nematicides, fungicides, growth-regulating substances or herbicides.

The agents for combating pests include, for example, phosphoric acid esters, carbamates, carboxylic acid esters, formamidines, tin compounds, and substances prepared by microorganisms among others. Preferred partners in the mixture are 1. from the group of phosphorus compounds acephate, azamethiphos, azinphos-ethyl, azinphos-methyl, bromophos, bromophos-ethyl, chlorfenvinphos, chlormephos, chlorpyrifos, chlorpyrifos-methyl, demeton, demeton-S-methyl, demeton-S-methylsulfphone, dialifos, diazinon, dichlorvos, dicrotophos, O,O-1,2,2,2-tetrachloroethylphosphorthioate (SD 203 304), dimethoate, disulfoton, EPN, ethion, ethoprophos, etrimfos, famphur, fenamiphos, fenitrothion, fensulfothion, fenthion, fonofos, formothion, heptenophos, isozophos, isothioate, isoxathion, malathion, methacrifos, methamidophos, methidation, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos-ethyl, pirimiphos-methyl, profenofos, propaphos, proetamphos, prothiofos, pyraclofos, pyridapenthion, quinalphos, sulprofos, temephos, terbufos, tetrachlorvinphos, thiometon, triazophos, trichlorphon and vamidothion;

2. from the group of carbamates aldicarb, 2-sec.-butylphenyl methylcarbamate (BPMC), carbaryl, carbofuran, carbosulfan, cloethocarb, benfuracarb, ethiofencarb, furathiocarb, isoprocarb, methomyl, 5-methyl-m-cumenylbutyryl methylcarbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135) and 1-methylthio(ethylideneamino) N-methyl-N-(morpholinothio)carbamate (UC 51717);

3. from the group of carboxylic acid esters allethrin, alphametrin, 5-benzyl-3-furylmethyl (E)-(1R)-cis-2,2-dimethyl-3-(2-oxothiolan-3-ylidenemethyl)cyclopropanecarboxylate, bioallethrin, bioallethrin ((S)-cyclopentyl isomer), bioresmethrin, biphenate, (RS)-1-cyano-1-(6-phenoxy-2-pyridyl)methyl (1RS)-trans-3-(4-tert.-butylphenyl)-2,2-dimethylcyclopropanecarboxylate (NCI 85193), cycloprothrin, cyfluthrin, cyhalothrin, cypermethrin, cyphenothrin, deltamethrin, empenthrin, esfenvalerate, fenfluthrin, fenpropathrin, fenvalerate, flucythrinate, flumethrin, fluvalinate (D isomer), permethrin, pheothrin ((R) isomer), d-pralethrin, pyrethrins (naturally occurring products), resmethrin, tefluthrin, tetramethrin and tralomethrin;

4. from the group of amidines amitraz and chlordimeform;

5. from the group of tin compounds cyhexatin and fenbutatin oxide;

6. others abamectin, Bacillus thuringiensis, bensultap, binapacryl, bromopropylate, buprofezin, camphechlor, cartap, chlorobenzilate, chlorfluazuron, 2-(4-(chlorophenyl)-4,5-diphenylthiophene (UBI-T 930), chlorfentezine, 2-naphthylmethyl cyclopropanecarboxylate (Ro 12-0470), cyromazin, N-(3,5-dichloro-4-(1,1,2,3,3,3-hexafluoro-1-propyloxy)phenyl)carbamoyl)-2-chlorobenzocarboximic acid ethyl ester, DDT, dicofol, N-(N-(3,5-dichloro-4-(1,1,2,2-tetrafluoroethoxy)-phenylamino)carbonyl)-2,6-difluorobenzamide (XRD 473), diflubenzuron, N-(2,3-dihydro-3-methyl-1,3-thiazol-2-ylidene)-2,4-xylidine, dinobuton, dinocap, endosulfan, ethofenprox, (4-ethoxyphenyl)(dimethyl)(3-(3-phenoxyphenyl)propyl)silane, (4-ethoxyphenyl)(3-(4-fluoro-3-phenoxyphenyl)propyl)dimethylsilane, fenoxycarb, 2-fluoro-5-(4-(4-ethoxyphenyl)-4-methyl-1-pentyl)diphenyl ether (MTI 800), granulose and nuclear polyhedral viruses, fenthiocarb, flubenzimine, flucycloxuron, flufenoxuron, gamma-HCH, hexythiazox, hydramethylnon (AC 217300), ivermectin, 2-nitrometyl-4,5-dihydro-6H-thiazine (SD 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam and triflumuron. The active compound content of the use forms prepared from the commercially available formulations can be from 0.00000001 to 100% by weight of active compound, preferably between 0.00001 and 1% by weight.

They are used in a customary manner appropriate for the use forms.

The active compounds according to the invention are also particularly suitable for combating endo- and ectoparasites in the veterinary medicine sector and in the field of animal husbandry.

The active compounds according to the invention are used here in a known manner, such as by oral application in the form of, for example, tablets, capsules, drinks or granules, by dermal application in the form of, for example, dipping, spraying, pouring on and spotting on and dusting on, and by parenteral administration in the form of, for example, injection.

In a pour-on formulation, the active compound is dissolved, emulsified or suspended in a suitable solvent or solvent mixture which is tolerated by the skin, if appropriate with the addition of further auxiliaries, and the solution, emulsion or suspension is applied to the skin of the animal to be treated with the aid of a suitable device (for example with the aid of a measuring beaker, a spray bottle or a metered syringe).

Pour-on formulations of insecticides and anthelmintics have already been disclosed in veterinary medicine (in this context, see Rogoff, W. M. and Kohler, P. H., J. Econ. Ent. 53, 814-817 (1960) and EP-A 45,242). The term "pour-on formulation" or "spot-on formulation" is familiar to the expert. Such a formulation is a liquid preparation which is suitable for so-called "pour-on application" and is poured onto the skin (pour-on treatment).

The novel compounds of the formula I according to the invention can accordingly also be particularly advantageously employed in animal husbandry (for example cattle, sheep, pigs and poultry, such as chickens, geese and the like). In a preferred embodiment of the invention, the novel compounds are administered orally to the animals, if appropriate in suitable formulations (see above) and if appropriate with the drinking water or feed. Since the excretion in the feces is effective, the development of insects in the feces of the animals can in this way be very easily prevented. The particular suitable dosages and formulations depend, in particular, on the species and development stage of the stock animals and also on the pressure of infestation, and can easily be determined and specified by the customary methods. The novel compounds can be used on cattle or sheep, for example, in dosages of 0.01 mg to 1 g/kg of body weight.

The following examples serve to illustrate the invention.

A. FORMULATION EXAMPLES a) A dusting agent is obtained by mixing 10 parts by weight of active compound and 90 parts by weight of talc, as the inert substance, and comminuting the mixture in an impact mill.

b) A wettable powder which is readily dispersible in water is obtained by mixing 25 parts by weight of active compound, 65 parts by weight of kaolin-containing quartz, as the inert substance, 10 parts by weight of potassium ligninsulfonate and 1 part by weight of sodium oleyl-methyl-taurate, as the wetting and dispersing agents, and grinding the mixture in a pinned disk mill.

c) A dispersion concentrate which is readily dispersible in water is prepared by mixing 40 parts by weight of active compound with 7 parts by weight of sulfosuccinic acid half-ester, 2 parts by weight of a sodium ligninsulfonate and 51 parts by weight of water and grinding the mixture to a fineness of less than 5 microns in a bead mill.

d) An emulsifiable concentrate can be prepared from 15 parts by weight of active compound, 75 parts by weight of cyclohexanone, as the solvent, and 10 parts by weight of oxyethylated nonylphenol (10 mol of ethylene oxide), as the emulsifier.

e) Granules can be prepared from 2 to 15 parts by weight of active compound and an inert granule carrier, such as attapulgite, pumice granules and/or quartz sand. A suspension of the wettable powder from Example b having a solids content of 30% is advantageously used, this is sprayed onto the surface of attapulgite granules and the components are dried and intimately mixed. The weight content of the wettable powder here is about 5% and that of the inert carrier about 95% of the finished granules.

B. CHEMICAL EXAMPLES a) Precursors 3,5-Dichloro-4-(2-(1,1,2,2,3,3-hexafluoropropoxy)-trifluoroethoxy)-aniline 116.00 g (0.84 mol) of potassium carbonate and then 153.00 g (0.62 mol) of trifluorovinyl 1,1,2,2,3,3-hexafluoropropyl ether were added to 100.00 g (0.56 mol) of 3,5-dichloro-4-aminophenol in 1100 ml of anhydrous acetonitrile and the mixture was stirred at 50° C. for 2 hours. The insoluble material was filtered off with suction and rinsed with methylene chloride and the filtrate was concentrated. The residue was dried under an oil pump vacuum.

Yield: 203.40 g (85% of theory) of oily product.

The compounds in Table 1 can also be prepared analogously to these instructions

TABLE 1

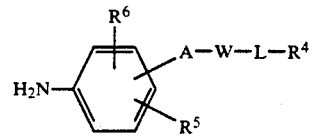

| Example | —A—W—L—R$^4$ | R$^5$ | R$^6$ | Melting point [°C.] |
|---|---|---|---|---|
| a | 4-F$_2$CH(CF$_2$)$_2$O—CHFCF$_2$O | H | H | Black oil |
| b | 4-F$_2$CH(CF$_2$)$_2$O—CHFCF$_2$O | 3-Cl | 5-Cl | " |
| c | 4-C$_3$F$_7$O—CHFCF$_2$O | 3-Cl | 5-Cl | " |
| d | 4-C$_3$F$_7$O—CF(CF$_3$)CF$_2$OCHFCF$_2$O | 3-Cl | 5-Cl | " |
| e | 2-F$_2$CH(CF$_2$)$_2$O—CHFCF$_2$O | H | H | Black oil |
| f | 2-F$_2$CH(CF$_2$)$_2$O—CHFCF$_2$O | 4-Cl | H | " |
| g | 2-F$_2$CH(CF$_2$)$_2$O—CHFCF$_2$O | 5-Cl | H | " |
| h | 3-F$_2$CH(CF$_2$)$_2$O—CHFCF$_2$O | H | H | " |

TABLE 1-continued

| | | | | |
|---|---|---|---|---|
| i | F$_3$C, O, OCHFCF$_2$O, F, F, F, F, O, F, CF$_3$ (cyclic structure) | 3-Cl | 5-Cl | " |
| j | C$_4$F$_9$CF=CFCF$_2$O, | 3-Cl | 5-Cl | " |
| j1 | 2-F$_2$CH(CF$_2$)$_2$O—CHFCF$_2$O | 5-NO$_2$ | H | " |
| j2 | 2-F$_2$CH(CF$_2$)$_2$O—CHFCF$_2$O | 4-CH$_3$ | H | " |
| j3 | 2-F$_2$CH(CF$_2$)$_2$O—CHFCF$_2$O | 5-CH$_3$ | H | " |
| j4 | 3-F$_2$CH(CF$_2$)$_2$O—CHFCF$_2$O | 4-Cl | H | " |
| j5 | 3-F$_2$CH(CF$_2$)$_2$O—CHFCF$_2$O | 6-Cl | H | " |
| | | | | $n_D(T[°C.])$ |
| j6 | 4-F$_2$CH(CF$_2$)$_2$O—CHFCF$_2$O | 2-CH$_3$ | H | 1,4150 (22,5) |
| j7 | 2-F$_2$CH(CF$_2$)$_2$O—CHFCF$_2$O | 4-CH$_3$, | 5-Cl | 1,4120 (23) |
| j8 | 4-F$_2$CH(CF$_2$)$_2$O—CHFCF$_2$O | 2,6-(CH$_3$)$_2$ | | 1,4213 (21) |
| j9 | 2-F$_2$CH(CF$_2$)$_2$O—CHFCF$_2$O | 5-CF$_3$ | H | 1,3895 (21) |
| j10 | 2-F$_2$CH(CF$_2$)$_2$O—CHFCF$_2$O | 3,5,6-Cl$_3$ | | 1,4372 (22) |
| j11 | 2-F$_2$CH(CF$_2$)$_2$O—CHFCF$_2$O | 3-CH$_3$ | H | Oil |
| J12 | 4-F$_2$CH(CF$_2$)$_2$O—CHFCF$_2$O | 2,3-(CH$_3$)$_2$ | | Oil |
| J13 | 3-F$_2$CH(CF$_2$)$_2$O—CHFCF$_2$O | 2,5-(CH$_3$)$_2$ | | Oil |
| J14 | 2-F$_2$CH(CF$_2$)$_2$O—CHFCF$_2$O | 3,5-(CH$_3$)$_2$ | | 1,4483 (23) |
| J15 | 3-F$_2$CH(CF$_2$)$_2$O—CHFCF$_2$O | 2-CH$_3$ | H | 1,4045 (23) |
| J16 | 2-CF$_3$—CFBrCF$_2$O—CHFCF$_2$O | 4-Cl | H | Oil |
| J17 | 2-CF$_3$—CFBrCF$_2$O—CHFCF$_2$O | 4-CH$_3$ | H | Oil |
| J18 | 4-F$_2$CBrCF$_2$O—CHFCF$_2$O | 3,5-Cl$_2$ | | Oil |
| J19 | 2-F$_2$CBrCF$_2$O—CHFCF$_2$O | 4-Cl | H | Oil |
| J20 | 2-F$_2$CBrCF$_2$O—CHFCF$_2$O | 4-CH$_3$ | H | Oil |
| J21 | 2-F$_2$CBrCF$_2$O—CHFCF$_2$O | 5-CH$_3$ | H | Oil |
| J22 | 4-F$_2$CBrCF$_2$O—CHFCF$_2$O | 2,6-(CH$_3$)$_2$ | | 1,4515 (26) |
| J23 | 2-F$_2$CBrCF$_2$O—CHFCF$_2$O | 5-CF$_3$ | H | 1,4122 (26) |
| J24 | 2-F$_2$CBrCF$_2$O—CHFCF$_2$O | 3.5,6-Cl$_3$ | | 1,4658 (26) |
| J25 | 4-F$_2$CBrCF$_2$O—CHFCF$_2$O | 2-CH$_3$ | H | 1,4380 (22) |
| J26 | 2-F$_2$CBrCF$_2$O—CHFCF$_2$O | 4-CH$_3$ | 5-Cl | 1,4653 (26) |
| J27 | 2-F$_2$CBrCF$_2$O—CHFCF$_2$O | 5-Cl | H | Oil |
| J28 | 4-F$_2$CH(CF$_2$)$_4$O—CHFCF$_2$O | 3.5-Cl$_2$ | | Oil |
| J29 | 2-F$_2$CH(CF$_2$)$_4$O—CHFCF$_2$O | 4-CH$_3$ | H | 1,3900 |
| J30 | 2-F$_2$CH(CF$_2$)$_4$O—CHFCF$_2$O | 4-Cl | H | Oil |
| J31 | 2-F$_2$CH(CF$_2$)$_4$O—CHFCF$_2$O | 5-Cl | H | Oil |
| J32 | 2-F$_2$CH(CF$_2$)$_4$O—CHFCF$_2$O | 5-CH$_3$ | H | 1,3947 (22) |
| J33 | 4-F$_2$CH(CF$_2$)$_4$O—CHFCF$_2$O | 2-CH$_3$ | H | 1,3945 (24) |
| J34 | 2-F$_2$CH(CF$_2$)$_4$O—CHFCF$_2$O | 4-CH$_3$ | 5-Cl | 1,4265 (28) |
| J35 | 2-F$_2$CH(CF$_2$)$_4$O—CHFCF$_2$O | 3,5,6-Cl$_3$ | | 1,4143 (26) |
| J36 | 4-F$_2$CH(CF$_2$)$_4$O—CHFCF$_2$O | H | H | Oil |
| J37 | 2-F$_2$CH(CF$_2$)$_4$O—CHFCF$_2$O | 5-CF$_3$ | H | 1,3723 (30) |
| J38 | 4-CF$_2$=CFO—(CF$_2$)$_6$—O—CHFCF$_2$O | 3,5-Cl$_2$ | | Oil |
| J39 | 2-CF$_2$=CFO—(CF$_2$)$_6$—O—CHFCF$_2$O | 5-CF$_3$ | H | 1,3962 (26) |
| J40 | 4-F$_3$C(CF$_2$)$_2$O—CHFCF$_2$O | 3,5-Cl$_2$ | | Oil |
| J41 | 2-F$_2$CH(CF$_2$)$_2$O—CHFCF$_2$S | H | H | 1,4501 (26,5) |
| J42 | 4-F$_2$CH(CF$_2$)$_2$O—CHFCF$_2$S | H | H | 1,4590 (24,5) |
| J43 | 3-F$_2$CH(CF$_2$)$_2$O—CHFCF$_2$S | H | H | 1,4441 (26) |
| J44 | 4-F$_2$CH(CF$_2$)$_2$O—CHFCF$_2$S | 2-F | H | 1,4420 (19) |
| J45 | 4-F$_2$CH(CF$_2$)$_2$O—CHFCF$_2$S | 2,5-CH$_3$ | | 1,4590 (22) |
| J46 | 4-F$_2$CH(CF$_2$)$_2$O—CHFCF$_2$S | 2-Br | H | 1,4966 (23,5) |
| J47 | 4-F$_2$CH(CF$_2$)$_2$O—CHFCF$_2$S | 2-CH$_3$O | H | 1,4825 (30) |
| J48 | 4-F$_2$CH(CF$_2$)$_2$O—CHFCF$_2$S | 2-CH$_3$ | H | 1,4628 (22) |
| J49 | 4-F$_2$CH(CF$_2$)$_2$O—CHFCF$_2$S | 2,5-Cl$_2$ | | 1,4721 (23) |
| J50 | 4-F$_2$CH(CF$_2$)$_2$O—CHFCF$_2$S | 2-F | 3-Cl | Oil |
| J51 | 4-F$_2$CH(CF$_2$)$_2$O—CHFCF$_2$S | 2-CN | H | Oil |
| J52 | 2-BrCF$_2$CF$_2$—O—CHF—CF$_2$S | H | H | Oil |
| J53 | 4-BrCF$_2$CF$_2$—O—CHF—CF$_2$S | H | H | Oil |
| J54 | 3-BrCF$_2$CF$_2$—O—CHF—CF$_2$S | H | H | Oil |
| J55 | 4-BrCF$_2$CF$_2$—O—CHF—CF$_2$S | 2,5-(CH$_3$)$_2$ | | 1,4404 (26) |
| J56 | 4-BrCF$_2$CF$_2$—O—CHF—CF$_2$S | 2-F | H | 1,4733 (29) |
| J57 | 4-BrCF$_2$CF$_2$—O—CHF—CF$_2$S | 2-Br | H | 1,5294 (26,5) |
| J58 | 4-BrCF$_2$CF$_2$—O—CHF—CF$_2$S | 2,5-Cl$_2$ | | 1,4989 (28) |
| J59 | 3-F$_2$CH—(CF$_2$)$_4$OCHF—CF$_2$S | H | H | 1,4257 (26) |
| J50 | 2-F$_2$CH—(CF$_2$)$_4$OCHF—CF$_2$S | H | H | 1,4320 (20) |
| J51 | 4-F$_2$CH—(CF$_2$)$_4$OCHF—CF$_2$S | H | H | Oil |
| J52 | 2-CF$_2$=CFO(CF$_2$)$_6$OCHFCF$_2$S | H | H | Oil |
| J53 | 4-CF$_2$=CFO(CF$_2$)$_6$OCHFCF$_2$S | H | H | Oil |

TABLE 1-continued

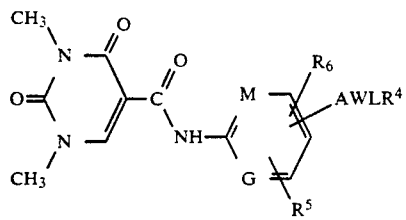

| Example | —A—W—L—R⁴ | R⁵ | R⁶ | M | G | n_D(T[°C.]) |
|---|---|---|---|---|---|---|
| J54 | 3-F₂CH(CF₂)₂O—CHFCF₂O | 5-CH₃ | H | N | N | Oil |
| J55 | 2-F₂CH(CF₂)₂O—CHFCF₂O | H | H | N | CH | Oil |

3,5-Dichloro-4-(2-(1,1,2,2,3,3-hexafluoropropoxy)-trifluoroethoxy)-phenyl isocyanate 42.60 g (0.10 mol) of 3,5-dichloro-4-(2-(1,1,2,2,3,3-hexafluoropropoxy)-trifluoroethoxy)-aniline and 50 g of phosgene in 250 ml of absolute toluene were slowly heated from 0° C. up to the reflux temperature. The excess phosgene was driven off with nitrogen and the solvent was concentrated. The resulting oil was employed without further purification.

Yield: 38.4 g (85% of theory).

TABLE 2

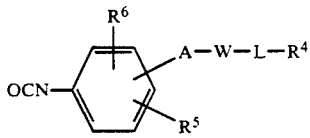

The compounds k–t can be prepared analogously to these instructions.

| Example | —A—W—L—R⁴ | R⁵ | R⁶ | Melting point [°C.] |
|---|---|---|---|---|
| k | 4-F₂CH(CF₂)₂O—CHFCF₂O | H | H | |
| l | 4-F₂CH(CF₂)₂O—CHFCF₂O | 3-Cl | 5-Cl | |
| m | 4-C₃F₇O—CHFCF₂O | 3-Cl | 5-Cl | |
| n | 4-C₃F₇O—CF(CF₃)CF₂OCHFCF₂O | 3-Cl | 5-Cl | |
| o | 2-F₂CH(CF₂)₂O—CHFCF₂O | H | H | |
| p | 2-F₂CH(CF₂)₂O—CHFCF₂O | 4-Cl | H | |
| q | 2-F₂CH(CF₂)₂O—CHFCF₂O | 5-Cl | H | |
| r | 3-F₂CH(CF₂)₂O—CHFCF₂O | H | H | |
| s | F₃C-C(F)(O-)-C(F)(F)-O-C(F)(CF₃)- (OCHFCF₂O) | 3-Cl | 5-Cl | |
| t | C₄F₉CF=CFCF₂O. | 3-Cl | 5-Cl | | b) End products 1,3-Dimethyl-5-(4-(2-(1,1,2,2,3,3-hexafluoropropoxy)-1,1,2-trifluoroethoxy)-phenylcarbamoyl)-barbituric acid (Example 1)

14.50 g (40.6 mmol) of 4-(2-(1,1,2,2,3,3-hexafluoropropoxy)-1,1,2-trifluoroethoxy)-aniline were added to 9.26 g (40.6 mmol) of 1,3-dimethyl-5-ethoxycarbonyl-barbituric acid in 100 ml of toluene, the mixture was stired under reflux for 2.5 hours and concentrated and the residue was recrystallized from methanol.

Yield: 9.50 g (48% of theory).

Melting point: 126° C.

1,3-Dimethyl-5-(3,5-dichloro-(4-(2-(1,1,2,2,3,3-hexafluoropropoxy)-1,1,2-trifluoroethoxy))-phenylcarbamoyl)barbituric acid (Example 4)

1.04 g (10.3 mmol) of triethylamine and then 9.25 g (20.5 mmol) of 3,5-dichloro-(4-(2-(1,1,2,2,3,3-hexafluoropropoxy)-1,1,2-trifluoroethoxy))-phenyl isocyanate were added to 3.20 g (20.5 mmol) of 1,3-dimethyl-barbituric acid in 40 ml of toluene at room temperature. The mixture was subsequently stirred at 40° C. for 2 hours, 200 ml of methylene chloride were added and the mixture was washed with 100 ml of 2N aqueous hydrochloric acid and several times with water. After drying over magnesium sulfate, the mixture was concentrated.

Yield: 11.30 (90% of theory).

Melting point: 137° C.

1,3-Dimethyl-5-(3,5-dichloro-(4-(2-(1,1,2,2,3,3,3-heptafluoropropoxy)-1,1,2-trifluoroethoxy))-phenylcarbamoyl)barbituric acid, triethylammonium salt (Example 15)

2.25 g (3.34 mmol) of 1,3-dimethyl-5-(3,5-dichloro-(4-(2-(1,1,2,2,3,3,3-heptafluoropropoxy)-1,1,2-trifluoroethoxy))-phenylcarbamoyl)-barbituric acid in 30 ml of acetonitrile were stirred with 0.38 g (3.7 mmol) of triethylamine at room temperature for 2 hours. The solution was concentrated and the residue was dried at 50° C. under an oil pump vacuum.

Yield: 2.90 g (98% of theory) of resinous product.

1,3-Dimethyl-5-(3,5-dichloro-(4-(2-(1,1,2,2,3,3-hexafluoropropoxy)-1,1,2-trifluoroethoxy))-phenylcarbamoyl)barbituric acid, ammonium salt (Example 5)

5.0 g (8.2 mmol) of 1,3-dimethyl-5-(3,5-dichloro-(4-(2-(1,1,2,2,3,3-hexafluoropropoxy)-1,1,2-trifluoroethoxy))phenylcarbamoyl)-barbituric acid were suspended in 50 ml of absolute acetonitrile. Ammonia was passed in at room temperature for 10 minutes and the mixture was stirred at 50° C. for 10 minutes. The precipitate which had separated out was filtered off with suction, washed with ether and dried.

Yield: 4.4 g (86% of theory).

Melting point: 133°–161° C.

The compounds of the formula I in the following Table 3 can be prepared analogously to these instructions.

TABLE 3

$$\text{(I)}$$

| Example | —A—W—L—R$^4$,R$^5$,R$^6$ | Y$^1$ | Melting point [°C.] |
|---|---|---|---|
| 1 | 4-F$_2$CH(CF$_2$)$_2$O—CHFCF$_2$O,H,H | OH | 126 |
| 2 | 4-F$_2$CH(CF$_2$)$_2$O—CHFCF$_2$O,H,H | O$^-$NH$_4^+$ | 145 |
| 3 | 4-F$_2$CH(CF$_2$)$_2$O—CHFCF$_2$O,H,H | O$^-$NH(C$_2$H$_5$)$_3^+$ | 134 |
| 4 | 4-F$_2$CH(CF$_2$)$_2$O—CHFCF$_2$O,3,5-Cl$_2$ | OH | 139 |
| 5 | 4-F$_2$CH(CF$_2$)$_2$O—CHFCF$_2$O,3,5-Cl$_2$ | O$^-$NH$_4^+$ | 133-161 |
| 6 | 4-F$_2$CH(CF$_2$)$_2$O—CHFCF$_2$O,3,5-Cl$_2$ | O$^-$NH(C$_2$H$_5$)$_3^+$ | Resin |
| 7 | 4-F$_2$CH(CF$_2$)$_2$O—CHFCF$_2$O,3,5-Cl$_2$ | O$^-$Li$^+$ | 136-139 |
| 8 | 4-F$_2$CH(CF$_2$)$_2$O—CHFCF$_2$O,3,5-Cl$_2$ | O$^-$Na$^+$ | >280 |
| 9 | 4-F$_2$CH(CF$_2$)$_2$O—CHFCF$_2$O,3,5-Cl$_2$ | O$^-$K$^+$ | >270 |
| 10 | 4-C$_3$F$_7$O—CHFCF$_2$O,3,5-Cl$_2$ | OH | 145 |
| 11 | 4-C$_3$F$_7$O—CHFCF$_2$O,3,5-Cl$_2$ | O$^-$NH$_4^+$ | 160-162 |
| 12 | 4-C$_3$F$_7$O—CHFCF$_2$O,3,5-Cl$_2$ | O$^-$NH(C$_2$H$_5$)$_3^+$ | Resin |
| 13 | 4-C$_3$F$_7$O—CF(CF$_3$)CF$_2$OCHFCF$_2$O,3,5-Cl$_2$ | OH | 124 |
| 14 | 4-C$_3$F$_7$O—CF(CF$_3$)CF$_2$OCHFCF$_2$O,3,5-Cl$_2$ | O$^-$NH$_4^+$ | 148 |
| 15 | 4-C$_3$F$_7$O—CF(CF$_3$)CF$_2$OCHFCF$_2$O,3,5-Cl$_2$ | O$^-$NH(C$_2$H$_5$)$_3^+$ | Resin |
| 16 | 2-F$_2$CH(CF$_2$)$_2$O—CHFCF$_2$O,H,H | OH | 144 |
| 17 | 2-F$_2$CH(CF$_2$)$_2$O—CHFCF$_2$O,H,H | O$^-$NH(C$_2$H$_5$)$_3^+$ | 93-94 |
| 18 | 2-F$_2$CH(CF$_2$)$_2$O—CHFCF$_2$O,H,H | O$^-$K$^+$ | >270 |
| 19 | 2-F$_2$CH(CF$_2$)$_2$O—CHFCF$_2$O,4-Cl,H | OH | 176,5 |
| 20 | 2-F$_2$CH(CF$_2$)$_2$O—CHFCF$_2$O,4-Cl,H | O$^-$NH(C$_2$H$_5$)$_3^+$ | |
| 21 | 2-F$_2$CH(CF$_2$)$_2$O—CHFCF$_2$O-4-Cl, H | O$^-$K$^+$ | |
| 22 | 2-F$_2$CH(CF$_2$)$_2$O—CHFCF$_2$O,5-Cl,H | OH | 121 |
| 23 | 2-F$_2$CH(CF$_2$)$_2$O—CHFCF$_2$O,5-Cl,H | O$^-$NH(C$_2$H$_5$)$_3^+$ | |
| 24 | 2-F$_2$CH(CF$_2$)$_2$O—CHFCF$_2$O,5-Cl,H | O$^-$K$^+$ | |
| 25 | 3-F$_2$CH(CF$_2$)$_2$O—CHFCF$_2$O,H,H | OH | 97 |
| 26 | 3-F$_2$CH(CF$_2$)$_2$O—CHFCF$_2$O,H,H | O$^-$NH(C$_2$H$_5$)$_3^+$ | Oil |
| 27 | 3-F$_2$CH(CF$_2$)$_2$O—CHFCF$_2$O,H,H | O$^-$K$^+$ | >270 |
| 28 | 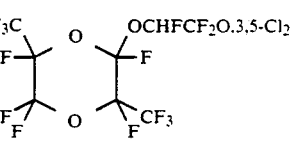 4-F$_3$C...OCHFCF$_2$O,3,5-Cl$_2$ | OH | 135 |
| 29 | 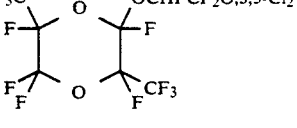 4-F$_3$C...OCHFCF$_2$O,3,5-Cl$_2$ | O$^-$NH(C$_2$H$_5$)$_3^+$ | resin |
| 30 | 4-C$_4$F$_9$CF=CFCF$_2$O,3,5-Cl$_2$ | OH | 114 |
| 31 | 4-F$_2$CH(CF$_2$)$_2$O—CHFCF$_2$O,3,5-Cl$_2$ | NH$_2$ | 174 |
| 32 | 3-F$_2$CH(CF$_2$)$_2$O—CHFCF$_2$O,4-Cl,H | OH | 92 |
| 33 | 3-F$_2$CH(CF$_2$)$_2$O—CHFCF$_2$O,4-Cl,H | O$^-$N(C$_2$H$_5$)$_3^+$ | Oil |
| 34 | " | O$^-$K$^+$ | |
| 35 | 3-F$_2$CH(CF$_2$)$_2$O—CHFCF$_2$O,6-Cl,H | OH | 99 |
| 36 | " | O$^-$N(C$_2$H$_5$)$_3^+$ | Oil |
| 37 | " | O$^-$K$^+$ | |
| 38 | 2-F$_2$CH(CF$_2$)$_2$O—CHFCF$_2$O, 5-NO$_2$,H | OH | 172 |
| 39 | " | O$^-$N(C$_2$H$_5$)$_3^+$ | |
| 40 | " | O$^-$K$^+$ | |
| 41 | 2-F$_2$CH(CF$_2$)$_2$O—CHFCF$_2$O,4-CH$_3$,H | OH | 156 |
| 42 | " | O$^-$N(C$_2$H$_5$)$_3^+$ | 128-145 |
| 43 | " | O$^-$Na$^+$ | >280 |
| 44 | " | O$^-$K$^+$ | >280 |
| 45 | 2-F$_2$CH(CF$_2$)$_2$O—CHFCF$_2$O,5-CH$_3$,H | OH | 152 |
| 46 | " | O$^-$N(C$_2$H$_5$)$^+$ | Oil 116-120 |
| 47 | " | O$^-$Na$^+$ | >280 |
| 48 | " | O$^-$K$^+$ | >280 |
| 49 | 4-CH$_3$O(CH$_2$)$_2$O,3,5-Cl$_2$ | OH | 168 |
| 50 | " | O$^-$N(C$_2$H$_5$)$_3^+$ | |
| 51 | 4-CH$_3$O(CH$_2$)$_2$O,H,H | OH | 170 |
| 52 | 4-C$_2$H$_5$O(CH$_2$)$_2$O,3,5-Cl$_2$ | OH | 154 |
| 53 | 4-C$_2$H$_5$O(CH$_2$)$_2$O,H,H | OH | 195-208 |
| 54 | 3-CH$_3$O(CH$_2$)$_2$O,H,H | OH | 140 |
| 55 | 3-C$_2$H$_5$O(CH$_2$)$_2$O,H,H | OH | 133 |
| 56 | 3-CH$_3$O(CH$_2$)$_2$O,2-CH$_3$,H | OH | |

TABLE 3-continued

| | | | |
|---|---|---|---|
| 57 | 3-$C_2H_5O(CH_2)_2O$,2-$CH_3$,H | OH | |
| 58 | 2-$CH_3O(CH_2)_2O$,H,H | OH | 138 |
| 59 | 2-$C_2H_5O(CH_2)_2O$,H,H | OH | 135 |
| 60 | 2-$CH_3O(CH_2)_2O$,5-Br,H | OH | 190 |
| 61 | 2-$C_2H_5O(CH_2)_2O$,5-Br,H | OH | 175 |
| 62 | 2-$CH_3O(CH_2)_2O$,3,5-Br$_2$ | OH | 179 |
| 63 | 2-$CH_3O(CH_2)_2O$,6-$CH_3$,H | OH | |
| 64 | 2-$C_2H_5O(CH_2)_2O$,6-$CH_3$,H | OH | |
| 65 | 4-$CH_3O(CH_2)_2O$,3-Cl,H | OH | 146 |
| 66 | 4-$C_2H_5O(CH_2)_2O$,3-Cl,H | OH | 126 |
| 67 | 2-$CH_3O(CH_2)_2O$,3-Cl,H | OH | 150 |
| 68 | 2-$C_2H_5O(CH_2)_2O$,3-Cl,H | OH | 118 |
| 69 | 4-$F_2CH(CF_2)_2O-CHFCF_2O$,2-$CH_3$,H | OH | 135 |
| 70 | 2-$F_2CH(CF_2)_2O-CHFCF_2O$,4-$CH_3$,5-Cl | OH | 137 |
| 71 | 4-$F_2CH(CF_2)_2O-CHFCF_2O$,2,6-($CH_3$) | OH | 139 |
| 72 | 2-$F_2CH(CF_2)_2O-CHFCF_2O$,5-$CF_3$,H | OH | 156 |
| 73 | 2-$F_2CH(CF_2)_2O-CHFCF_2O$,3,5,6-$Cl_3$ | OH | 120 |
| 74 | 2-$F_2CH(CF_2)_2O-CHFCF_2O$,3-$CH_3$,H | OH | 137 |
| 75 | 4-$F_2CH(CF_2)_2O-CHFCF_2O$,2,3-($CH_3$)$_2$ | OH | 130 |
| 76 | 4-$F_2CH(CF_2)_2O-CHFCF_2O$,2,5-($CH_3$)$_2$ | OH | 129 |
| 77 | 2-$F_2CH(CF_2)_2O-CHFCF_2O$,3,5-($CH_3$)$_2$ | OH | 150 |
| 78 | 2-$CF_3-CFBr-CF_2O-CHFCF_2O$,4-Cl,H | OH | 115 |
| 79 | 2-$CF_3-CFBr-CF_2O-CHFCF_2O$,4-$CH_3$,H | OH | 137 |
| 80 | 4-$F_2CBrCF_2O-CHFCF_2O$,3,5-$Cl_2$ | OH | 127 |
| 81 | 2-$F_2CBrCF_2O-CHFCF_2O$,4-Cl,H | OH | 141 |
| 82 | 2-$F_2CBrCF_2O-CHFCF_2O$,4-$CH_3$,H | OH | 139 |
| 83 | 2-$F_2CBrCF_2O-CHFCF_2O$,5-$CH_3$,H | OH | 146 |
| 84 | 2-$F_2CBrCF_2O-CHFCF_2O$,2,6-($CH_3$)$_2$ | OH | 113 |
| 85 | 2-$F_2CBrCF_2O-CHFCF_2O$,5-$CF_3$,H | OH | 157 |
| 86 | 2-$F_2CBrCF_2O-CHFCF_2O$,3,5,6-$Cl_3$ | OH | 146 |
| 87 | 4-$F_2CBrCF_2O-CHFCF_2O$,2-$CH_3$,H | OH | 118 |
| 88 | 2-$F_2CBrCF_2O-CHFCF_2O$,4-$CH_3$,5-Cl | OH | 159 |
| 89 | 2-$F_2CBrCF_2O-CHFCF_2O$,5-Cl,H | OH | 172 |
| 90 | 4-$F_2CH(CF_2)_4O-CHFCF_2O$,3,5-$Cl_2$ | OH | 126 |
| 91 | 2-$F_2CH(CF_2)_4O-CHFCF_2O$,4-$CH_3$,H | OH | 130 |
| 92 | 2-$F_2CH(CF_2)_4O-CHFCF_2O$,4-Cl,H | OH | 102 |
| 93 | 2-$F_2CH(CF_2)_4O-CHFCF_2O$,5-Cl,H | OH | 162 |
| 94 | 2-$F_2CH(CF_2)_4O-CHFCF_2O$,5-$CH_3$,H | OH | 139 |
| 95 | 4-$F_2CH(CF_2)_4O-CHFCF_2O$,2-$CH_3$,H | OH | 110 |
| 96 | 2-$F_2CH(CF_2)_4O-CHFCF_2O$,4-$CH_3$,5-Cl | OH | 114 |
| 97 | 2-$F_2CH(CF_2)_4O-CHFCF_2O$,3,5,6-$Cl_3$ | OH | 138 |
| 98 | 4-$F_2CH(CF_2)_4O-CHFCF_2O$,H,H | OH | 93 |
| 99 | 2-$F_2CH(CF_2)_4O-CHFCF_2O$,5-$CF_3$,H | OH | 138 |
| 100 | 4-$CF_2=CFO-(CF_2)_6-O-CHFCF_2O$,3,5-$Cl_2$ | OH | 192 |
| 101 | 2-$CF_2=CFO-(CF_2)_6-O-CHFCF_2O$,5-$CF_3$,H | OH | 215 |
| 102 | 4-$F_3C(CF_2)_2O-CHFCF_2O$,3,5-$Cl_2$ | $NH_2$ | 192 |
| 103 | 2-$F_2CH(CF_2)_2O-CHFCF_2S$,H,H | OH | 121 |
| 104 | 4-$F_2CH(CF_2)_2O-CHFCF_2S$,H,H | OH | 119 |
| 105 | 3-$F_2CH(CF_2)_2O-CHFCF_2S$,H,H | OH | 102 |
| 106 | 4-$F_2CH(CF_2)_2O-CHFCF_2S$,2-F,H | OH | 114 |
| 107 | 4-$F_2CH(CF_2)_2O-CHFCF_2S$,2,5-($CH_3$)$_2$ | OH | 132 |
| 108 | 4-$F_2CH(CF_2)_2O-CHFCF_2S$,2-Br,H | OH | 96 |
| 109 | 4-$F_2CH(CF_2)_2O-CHFCF_2S$,2-$CH_3O$,H | OH | 144 |
| 110 | 4-$F_2CH(CF_2)_2O-CHFCF_2S$,2-$CH_3$,H | OH | 111 |
| 111 | 4-$F_2CH(CF_2)_2O-CHFCF_2S$,2,5-$Cl_2$ | OH | 145 |
| 112 | 4-$F_2CH(CF_2)_2O-CHFCF_2S$,2-F,3-Cl | OH | 114 |
| 113 | 4-$F_2CH(CF_2)_2O-CHFCF_2S$,2-CN,H | OH | 105 |
| 114 | 2-$BrCF_2CF_2O-CHF-CF_2S$,H,H | OH | 85-87 |
| 115 | 4-$BrCF_2CF_2O-CHF-CF_2S$,H,H | OH | 102-104 |
| 116 | 3-$BrCF_2CF_2O-CHF-CF_2S$,H,H | OH | 89 |
| 117 | 4-$BrCF_2CF_2O-CHF-CF_2S$,2,5-($CH_3$)$_2$ | OH | 132 |
| 118 | 4-$BrCF_2CF_2O-CHF-CF_2S$,2-F,H | OH | 107 |
| 119 | 4-$BrCF_2CF_2O-CHF-CF_2S$,2-Br,H | OH | 124 |
| 120 | 4-$BrCF_2CF_2O-CHF-CF_2S$,2,5-$Cl_2$ | OH | 132 |
| 121 | 3-$F_2CH-(CF_2)_4OCHF-CF_2S$,H,H | OH | 102 |
| 122 | 2-$F_2CH-(CF_2)_4OCHF-CF_2S$,H,H | OH | 70 |
| 123 | 4-$F_2CH-(CF_2)_4OCHF-CF_2S$,H,H | OH | 84 |
| 124 | 2-$CF_2=CFO(CF_2)_6OCHFCF_2S$,H,H | OH | 140 |
| 125 | 4-$CF_2=CFO(CF_2)_6OCHFCF_2S$,H,H | OH | 168 |
| 126 | 3-$C_2H_5O(CH_2)_2O$,2-$CH_3$,H | OH | Harz |
| 127 | 2-$C_2H_5O(CH_2)_2O$,3,5-$Br_2$ | OH | 158 |
| 128 | 4-$C_4H_9O(CH_2)_2O$,H,H | OH | 119 |
| 129 | 2-$C_4H_9O(CH_2)_2O$,3,5-$Br_2$ | OH | 137 |
| 130 | 4-$C_4H_9O(CH_2)_2O$,3,5-$Cl_2$ | OH | 132 |
| 131 | 4-$CH_3O-(CH_2)_2-(CH_2)_2O$,H,H | OH | 134-135 |
| 132 | 4-$CH_3O-(CH_2)_2-(CH_2)_2O$,3,5-$Cl_2$ | OH | 135 |
| 133 | 2-$CH_3O-(CH_2)_2-(CH_2)_2O$,3,5-$Br_2$ | OH | 132 |
| 134 | 4-$CH_3O-CH(CH_3)(CH_2)_2O$,H,H | OH | 115 |
| 135 | 4-$CH_3O-CH(CH_3)(CH_2)_2O$,3,5-$Cl_2$ | OH | 176 |
| 136 | 4-$CH_3O-CH_2CH(CH_3)O$,H,H | OH | 110-112 |
| 137 | 4-$CH_3O-CH_2CH(CH_3)O$,3,5-$Cl_2$ | OH | 178 |
| 138 | 2-$CH_3O-CH_2CH(CH_3)O$,3,5-$Br_2$ | OH | 169 |

TABLE 3-continued

| | | | |
|---|---|---|---|
| 139 | 4-CH₃O(CH₂)₂O—(CH₂)₂S,H,H | OH | 85 |
| 140 | 4-CH₃O(CH₂)₂O—(CH₂)₂S,2-Br,H | OH | |
| 141 | 4-CH₃O(CH₂)₂S,H,H | OH | 96 |
| 142 | 4-C₂H₅O(CH₂)₂S,H,H | OH | 86 |
| 143 | 4-C₄H₉O(CH₂)₂S,H,H | OH | 86 |
| 144 | 4-CH₃O—CH(CH₃)CH₂S,H,H | OH | 91 |

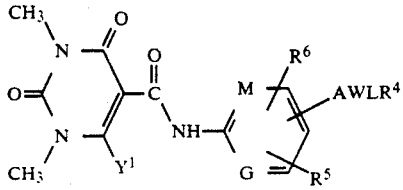

| Example | —A—W—L—R⁴,R⁵,R⁶ | M | G | Y¹ | Melting point [°C.] |
|---|---|---|---|---|---|
| 145 | 3-F₂CH(CF₂)₂O—CHFCF₂O,H,H | N | C | OH | 142 |
| 146 | 3-F₂CH(CF₂)₂O—CHFCF₂O,5-CH₃,H | N | N | OH | |
| 147 | 3-CH₃O(CH₂)₂O,H,H | N | C | OH | |
| 148 | 3-C₂H₅O(CH₂)₂O,H,H | N | C | OH | |
| 149 | 3-CH₃O(CH₂)₂O,5-CH₃,H | N | N | OH | |
| 150 | 3-C₂H₅O(CH₂)₂O,5-CH₃,H | N | N | OH | |
| 151 | 3-F₂CH(CF₂)₂O—CHFCF₂O,5-CH₃,H | N | N | OH | 175–202 |
| 152 | 2-F₂CH(CF₂)₂O—CHFCF₂O,H,H | N | CH | OH | 142 |
| 153 | 2-F₂CH(CF₂)₂O—CHFCF₂O,H,H | N | CH | O⁻NH(C₂H₅)₃+ | Resin |

C. BIOLOGICAL EXAMPLES:

EXAMPLE 1

Lucilia test

The substances are dissolved in a mixture consisting of dimethylformamide (85 g), ®Emulsogen (7 g) and ®Arkopal N 60 (3 g) so that dilution series containing active compound concentrations of 10,000/1,000 ppm are obtained. 1 ml portions of these solutions are intimately mixed with 9 g of finely ground meat, so that in the end meat having active compound concentrations of 1,000/100 ppm is available. As a control, 1 ml of solvent is added to 9 g of meat.

20 freshly emerged larvae of Lucilia cuprina are in each case added to the larval nutrient media thus prepared. After 72 hours, when the larvae I have developed to the pupation-ready larvae III in the control medium, the mortality rate is determined. In this test, the compounds according to Examples 3, 4, 6, 10, 12, 28 and 29 (Table 3) brought about 100% destruction of the larvae at an active compound concentration of 100 ppm.

EXAMPLE 2

Nematode test; in vitro

In the in vitro experiments, nematodes are kept in a culture medium to which the test substance is added for up to 5 days. The motility of the nematodes and their reproduction on the 6th day of the experiment is investigated and measured in comparison with untreated control cultures.

EXAMPLE 3

Nematode test; in vivo

In nematode experiments, laboratory rodents, dogs (±10 kg body weight) or lambs (±20 kg body weight) are infected with their natural or adapted nematodes, and when the prepatency period has elapsed the egg excretion is checked coproscopically several times until it has stabilized. The animals are then treated with the test substance, once or several times, by various administration routes and at various dosages. A maximum of 400 mg/kg of body weight is administered to laboratory rodents and 50 mg/kg of body weight to large animals. The result of treatment is checked coproscopically up to four weeks after the administration, and if the egg excretion has been reduced by more than 90%, a helminthological section is performed and the worm loads are compared with those of an untreated control group.

EXAMPLE 4

Nematode test

Lambs weighing ±20 kg of body weight are infected orally with metacercaria of the trematode Fasciola hepatica. When the prepatency period has elapsed, the level of excretion of Fasciola eggs is repeatedly checked coproscopically; when the egg excretion has stabilized, medicamentous treatment is performed by an administration route which changes from case to case. The dosage is likewise variable, is administered once or several times and is a maximum of 50 mg/kg of body weight. The success is checked coproscopically up to four weeks after administration, and in the case of an egg reduction of more than 90% a helminthological section is performed. The evaluation is performed as a "controlled test", that is to say in comparison with an untreated experimental group.

| Example according to Table 3 | Anthelmintic activity Fasciola hepatica 1 × 10 to 50 mg/kg of body weight perorally | Gastrointestinal nematodes 1 × 10 to 50 mg/kg of body weight perorally and/or subcutaneously | In vitro screening of helminths motility/reproduction | |
| --- | --- | --- | --- | --- |
| 4 | +++ | +++ | +++ | +++ |
| 10 | +++ | +++ | +++ | +++ |
| 13 | +++ | + | + | ++ |
| 30 | +++ | ++ | +++ | +++ |

+++ = action very potent, pronounced
++ = action potent
+ = action significant

We claim:
1. A compound of the formula I, a tautomeric form thereof of the formula Ia, a stereoisomer thereof or a mixture of these forms

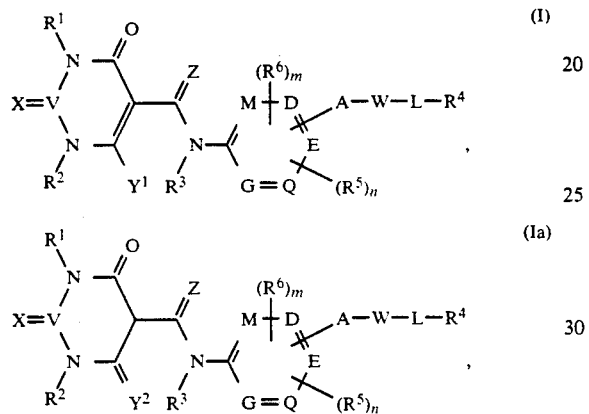

wherein $R^1$ and $R^2$ independently of one another denote $(C_1-C_6)$-alkyl, $(C_2-C_6)$-alkenyl or $(C_2-C_6)$-alkynyl; all of which can be substituted by one to thirteen halogen atoms or which may optionally be mono-, di- or trisubstituted by a radical from the group consisting of $(C_1-C_4)$-alkoxy, $(C_1-C_4)$-alkoxycarbonyl, $(C_2-C_4)$-alkylsulfenyl, $(C_1-C_4)$-alkylsulfinyl, $(C_1-C_4)$-alkylsulfonyl, di$(C_2-C_4)$-alkylamino, cyano, sulfo, nitro, hydroxyl, carboxyl, phenyl or phenyoxy, it being possible for the last two radicals mentioned to be mono-, di- or trisubstituted by a radical from the group consisting of halogen, $(C_1-C_4)$-alkyl, $(C_1-C_4)$-alkoxy, $(C_1-C_4)$-alkylcarbonyl, $(C_1-C_4)$-alkoxycarbonyl, $(C_1-C_4)$-alkylsulfenyl, $(C_1-C_4)$-alkylsulfinyl, $(C_1-C_4)$-alkylsulfonyl, halo$(C_1-C_4)$-alkoxy having in the last case one to nine halogen atoms; di$(C_1-C_4)$alkylamino, cyano, sulfo and nitro; $(C_1-C_4)$-alkoxy, $(C_1-C_4)$-alkylsulfonyl, $(C_1-C_4)$-alkylcarbonyl, cyano, phenylsulfonyl or phenylcarbonyl, it being possible for the last two radicals mentioned to be substituted by one to three radicals from the group consisting of halogen, $(C_1-C_4)$-alkyl, $(C_1-C_4)$-alkoxy, halo$(C_1-C_4)$-alkoxy having in the last case one to nine halogen atoms; and nitro; phenyl which can be substituted by one to three radicals from the group consisting of halogen, $(C_1-C_4)$-alkyl, $(C_1-C_4)$-alkoxy, $(C_1-C_4)$-alkylcarbonyl, $(C_1-C_4)$-alkylsulfenyl, $(C_1-C_4)$-alkylsulfinyl, $(C_1-C_4)$-alkylsulfonyl, halo$(C_1-C_4)$-alkyl, halo$(C_1-C_4)$-alkoxy having in the last two cases one to nine halogen atoms; di$(C_1-C_4)$-alkylamino, cyano, sulfo, nitro and phenoxy, which is optionally substituted by one to three radicals from the group consisting of halogen, $(C_1-C_4)$-alkyl and $(C_1-C_4)$-alkoxy, $R^3$ denotes hydrogen or $(C_1-C_6)$-alkyl; or phenyl, which can be substituted by one to three radicals from the group consisting of halogen, $(C_1-C_4)$-alkyl, $(C_1-C_4)$-alkoxy, $(C_1-C_4)$-alkylcarbonyl, $(C_1-C_4)$-alkoxycarbonyl, $(C_1-C_4)$-alkylsulfenyl, $(C_1-C_4)$-alkylsulfonyl, halo$(C_1-C_4)$-alkyl, halo$(C_1-C_4)$-alkoxy having one to nine halogen atoms; di$(C_1-C_4)$alkylamino, cyano, sulfo, nitro and phenoxy, which is optionally substituted by one to three radicals from the group consisting of halogen, $(C_1-C_4)$-alkyl and $(C_1-C_4)$-alkoxy, $R^4$ denotes hydrogen, $(C_1-C_6)$-alkyl, $(C_2-C_6)$-alkenyl or $(C_2-C_6)$-alkynyl, all of which can be substituted by one to nine halogen atoms or which may optionally be mono-, di- or trisubstituted by a radical from the group consisting of $(C_1-C_6)$-alkoxy, halo$(C_1-C_6)$-alkoxy, $(C_1-C_6)$-alkoxycarbonyl, halo$(C_1-C_6)$-alkoxycarbonyl, $(C_1-C_6)$-alkylsulfenyl, $(C_1-C_6)$-alkylsulfinyl, $(C_1-C_6)$-alkylsulfonyl, di$(C_1-C_6)$-alkylamino, cyano, sulfo, nitro, hydroxyl, carboxyl, phenyl and phenoxy, it being possible for the last two radicals mentioned to be mono-, di- or trisubstituted by a radical from the group consisting of halogen, $(C_1-C_4)$-alkyl, halo$(C_1-C_4)$-alkyl having in the last case one to nine halogen atoms; $(C_1-C_4)$-alkoxy, $(C_1-C_4)$-alkylcarbonyl, halo$(C_1-C_4)$-alkylcarbonyl, $(C_1-C_4)$-alkoxycarbonyl, halo$(C_1-C_4)$-alkoxycarbonyl, $(C_1-C_4)$-alkylsulfenyl, $(C_1-C_4)$-alkylsulfinyl, $(C_1-C_4)$-alkylsulfonyl, sulfato, halo$(C_1-C_4)$-alkoxy having in the last case one to nine halogen atoms; di$(C_1-C_4)$-alkylamino, cyano, sulfo and nitro; $(C_1-C_6)$-alkylsulfonyl, $(C_1-C_6)$-alkylcarbonyl, halo$(C_1-C_6)$-alkylsulfonyl, halo$(C_1-C_6)$-alkylcarbonyl, mono- or di$(C_1-C_4)$-alkylcarbamoyl, cyano, phenylsulfonyl, phenylcarbonyl or phenylcarbamoyl, it being possible for the last three radicals mentioned to be substituted by one to three radicals from the group consisting of halogen, $(C_1-C_4)$-alkyl, halo$(C_1-C_4)$-alkyl, $(C_1-C_4)$-alkoxy, halo$(C_1-C_4)$-alkoxy, $(C_1-C_4)$-alkylcarbonyl, halo$(C_1-C_4)$-alkylcarbonyl, $(C_1-C_4)$-alkoxycarbonyl, halo$(C_1-C_4)$-alkoxycarbonyl, $(C_1-C_4)$-alkylsulfenyl, $(C_1-C_4)$-alkylsulfinyl, $(C_1-C_4)$-alkylsulfonyl, di$(C_1-C_4)$-alkylamino, cyano, sulfo and nitro; or phenyl, which can be substituted by one to three radicals from the group consisting of halogen, $(C_1-C_4)$-alkyl, $(C_1-C_4)$-alkoxy, $(C_1-C_4)$-alkylcarbonyl, $(C_1-C_4)$-alkoxycarbonyl, $(C_1-C_4)$-alkylsulfenyl, $(C_1-C_4)$-alkylsulfinyl, $(C_1-C_4)$-alkylsulfonyl, halo$(C_1-C_4)$-alkyl, halo$(C_1-C_4)$-alkoxy having in the last two cases one to nine halogen atoms; di$(C_1-C_4)$-alkylamino, cyano, sulfo, nitro and phenoxy, which is optionally substituted by one to three radicals from the group consisting of halogen, $(C_1-C_4)$-alkyl and $(C_1-C_4)$-alkoxy, $R^5$ and $R^6$ independently of one another denote halogen, $(C_1-C_4)$-alkyl, $(C_1-C_4)$-alkoxy, $(C_1-C_4)$-alkylcarbonyl, $(C_1-C_4)$-alkoxycarbonyl, $(C_1-C_4)$-alkylsulfenyl, $(C_1-C_4)$-alkylsulfinyl, $(C_1-C_4)$-alkylsulfonyl, halo$(C_1-C_4)$-alkyl, halo$(C_1-C_4)$-alkoxy having in the last two cases one to nine halogen atoms; di$(C_1-C_4)$-alkylamino, cyano, sulfo or nitro, A, X and Z independently of one another denote oxygen, sulfur, sulfinyl, sulfonyl or nitrogen, which can be substituted by $(C_1-C_4)$-alkyl, L denotes oxygen, sulfur, sulfinyl, sulfonyl or nitrogen, which can be substituted by $(C_1-C_4)$-alkyl;

M, D, E, denote carbon,

V denotes carbon,

W denotes $(C_1-C_{10})$-alkylene or halo$(C_1-C_{10})$-alkylene, which can be substituted by one to five radicals from the group consisting of $(C_1-C_4)$-alkyl, holo$(C_1-C_4)$-alkyl, $(C_1-C_4)$-alkoxy, halo$(C_1-C_4)$-alkoxy, cyano or nitro, $Y^1$ denotes H, halogen, $(C_1-C_4)$-alkyl, amino, $(C_1-C_4)$-alkylamino, di$(C_1-C_4)$-alkylamino or $Y^2$ denotes oxygen or sulfur, or nitrogen which can be substituted by $(C_1-C_4)$-alkyl, and n and m independently of one another denote the numbers 0 to 4, or a salt thereof which can be employed in agriculture or is physiologically tolerated.

2. A compound of the formula I or Ia as claimed in claim 1, in which $R^1$ and $R^2$ independently of one another denote $(C_1-C_6)$-alkyl, $(C_2-C_6)$-alkenyl or $(C_2-C_6)$-alkynyl; all of which can be substituted by one to thirteen halogen atoms or which may optionally be mono-, di- or trisubstituted by a radical from the group consisting of $(C_1-C_4)$-alkoxy, $(C_1-C_4)$-alkoxycarbonyl, $(C_1-C_4)$-alkylsulfenyl, di$(C_1-C_4)$-alkylamino, cyano, sulfo, nitro, hydroxyl, carboxyl, phenyl or phenoxy, it being possible for the last two radicals mentioned to be mono-, di- or trisubstituted by a radical from the group consisting of halogen, $(C_1-C_4)$-alkyl, $(C_1-C_4)$-alkoxy, $(C_1-C_4)$-alkylcarbonyl, $(C_1-C_4)$-alkoxycarbonyl, $(C_1-C_4)$-alkylsulfenyl, $(C_1-C_4)$-alkylsulfinyl, $(C_1-C_4)$-alkylsulfonyl, halo$(C_1-C_4)$-alkoxy having in the last case one to nine halogen atoms; di$(C_1-C_4)$-alkylamino, cyano, sulfo and nitro, $R^3$ denotes hydrogen or $(C_1-C_6)$-alkyl, $R^4$ denotes hydrogen, $(C_1-C_6)$-alkyl, $(C_2-C_6)$-alkenyl or $(C_2-C_6)$-alkynyl, all of which can be substituted by one to nine halogen atoms or which also may optionally be mono-, di- or trisubstituted by a radical from the group consisting of $(C_1-C_6)$-alkoxy, halo$(C_1-C_6)$-alkoxy, $(C_1-C_6)$-alkoxycarbonyl, halo$(C_1-C_6)$-alkoxycarbonyl, $(C_1-C_6)$-alkylsulfenyl, cyano, sulfo, nitro, hydroxyl, carboxyl, phenyl and phenoxy, it being possible for the last three radicals mentioned to be mono- di- or trisubstitued by a radical from the group consisting of halogen, $(C_1-C_4)$-alkyl, halo$(C_1-C_4)$-alkyl, $(C_1-C_4)$-alkoxy, halo$(C_1-C_4)$-alkoxy, $(C_1-C_4)$-alkylcarbonyl, halo$(C_1-C_4)$-alkylcarbonyl, $(C_1-C_4)$-alkoxycarbonyl, halo$(C_1-C_4)$-alkoxycarbonyl, $(C_1-C_4)$-alkylsulfenyl, $(C_1-C_4)$-alkylsulfinyl, $(C_1-C_4)$-alkylsulfonyl, di$(C_1-C_4)$-alkylamino, cyano, sulfo and nitro; $(C_1-C_6)$-alkylsulfonyl, $(C_1-C_6)$-alkylcarbonyl, halo$(C_1-C_6)$-alkylsulfonyl, halo$(C_1-C_6)$-alkylcarbonyl, mono-, di$(C_1-C_4)$-alkylcarbamoyl, cyano, phenylsulfonyl, phenylcarbonyl or phenylcarbamoyl, it being possible for the last three radicals mentioned to be substituted by one to three radicals from the group consisting of halogen, $(C_1-C_4)$-alkyl, halo$(C_1-C_4)$-alkyl, $(C_1-C_4)$-alkoxy, halo$(C_1-C_4)$-alkoxy, $(C_1-C_4)$-alkylcarbonyl, halo$(C_1-C_4)$-alkylcarbonyl, $(C_1-C_4)$-alkoxycarbonyl, halo$(C_1-C_4)$-alkoxycarbonyl, $(C_1-C_4)$-alkylsulfenyl, $(C_1-C_4)$-alkylsulfinyl, $(C_1-C_4)$-alkylsulfonyl, di$(C_1-C_4)$-alkylamino, cyano, sulfo and nitro, $R^5$ and $R^6$ independently of one another denote halogen, $(C_1-C_4)$-alkyl, $(C_1-C_4)$-alkoxy, $(C_1-C_4)$-alkylcarbonyl, $(C_1-C_4)$-alkoxycarbonyl, $(C_1-C_4)$-alkylsulfenyl, halo$(C_1-C_4)$-alkoxy having in the last case one to nine halogen atoms, di$(C_1-C_4)$-alkylamino, cyano, sulfo and nitro, A, X and Z independently of one another denote oxygen, sulfur, sulfinyl or sulfonyl, L denotes oxygen, sulfur, sulfinyl, sulfonyl or nitrogen, which can be substituted by $(C_1-C_4)$-alkyl;

M, D, E, independently of one another denote carbon

Q and G,

V denotes carbon,

W denotes $(C_1-C_{10})$-alkylene or halo$(C_1-C_{10})$-alkylene, which can be substituted by one to five radicals from the group consisting of $(C_1-C_4)$-alkyl, halo$(C_1-C_4)$-alkyl, $(C_1-C_4)$-alkoxy, halo$(C_1-C_4)$-alkoxy, cyano and nitro, $Y^1$ denotes H, halogen, $(C_1-C_4)$-alkyl, amino, $(C_1-C_4)$-alkylamino, di$(C_1-C_4)$-alkylamino or hydroxyl, $Y^2$ denotes oxygen or sulfur, or nitrogen, which can be substituted by $(C_1-C_4)$-alkyl, and n and m independently of one another denote the number 0 to 4, or a salt thereof which can be employed in agriculture or is physiologically tolerated.

3. A compound of the formula I or Ia as claimed in claim 1, in which $R^1$ and $R^2$ independently of one another denote $(C_1-C_6)$-alkyl, $(C_2-C_6)$-alkenyl or $(C_2-C_6)$-alkynyl; all of which can be substituted by one to thirteen halogen atoms or which may optionally be $(C_1-C_4)$-alkoxy, $(C_1-C_4)$-alkoxycarbonyl or $(C_1-C_4)$-alkylsulfenyl, $R^3$ denotes hydrogen or $(C_1-C_6)$-alkyl, $R^4$ denotes hydrogen, $(C_1-C_6)$-alkyl, $(C_2-C_6)$-alkenyl or $(C_2-C_6)$-alkynyl, all of which can be substituted by one to nine halogen atoms or which may optionally be mono-, di- or trisubstituted by a radical from the group consisting of $(C_1-C_6)$-alkoxy, halo$(C_1-C_6)$-alkoxy, $(C_1-C_6)$-alkoxycarbonyl, halo$(C_1-C_6)$-alkoxycarbonyl, $(C_1-C_6)$-alkylsulfenyl, $(C_1-C_6)$-alkylsulfinyl, di$(C_1-C_6)$-alkylamino, cyano, sulfo, nitro, hydroxyl and carboxyl; or $(C_1-C_6)$-alkylsulfonyl, $(C_1-C_6)$-alkylcarbonyl, halo$(C_1-C_6)$-alkylsulfonyl, halo$(C_1-C_6)$-alkylcarbonyl or mono- or di$(C_1-C_4)$-alkylcarbamoyl, $R^5$ and $R^6$ independently of one another denote halogen, $(C_1-C_4)$-alkyl, $(C_1-C_4)$-alkoxy, $(C_1-C_4)$-alkylcarbonyl, $(C_1-C_4)$-alkoxycarbonyl, $(C_1-C_4)$-alkylsulfenyl, halo$(C_1-C_4)$-alkoxy having in the last case one to nine halogen atoms; di$(C_1-C_4)$-alkylamino, cyano, sulfo or nitro, A, X and Z independently of one another denote oxygen or sulfur, L denotes oxygen, sulfur or nitrogen, which can be substituted by $(C_1-C_4)$-alkyl;

M, D, E, denote

Q and G carbon,

V denotes carbon,

W denotes $(C_1-C_{10})$-alkylene or halo$(C_1-C_{10})$-alkylene, which can be substituted by one to five radicals from the group comprising $(C_1-C_4)$-alkyl, halo$(C_1-C_4)$-alkyl, $(C_1-C_4)$-alkoxy or halo$(C_1-C_4)$-alkoxy, $Y^1$ denotes H, amino or hydroxyl, $Y^2$ denotes oxygen or sulfur, or nitrogen, which can be substituted by $(C_1-C_4)$-alkyl, and n and m independently of one another denote the numbers 0 to 4, or a salt thereof which can be employed in agriculture or is physiologically tolerated.

4. The compound of the formula I

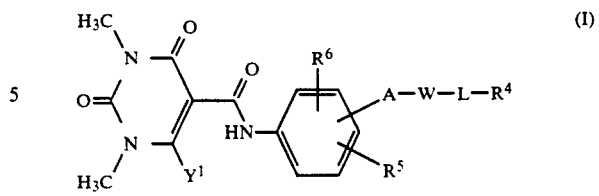

wherein $—A—W—L—R^4, R^5, R^6$ is $4—F_2CH(CF_2)_2O—CHFCF_2O, 3,5—Cl_2$, and wherein $Y^1$ is OH.

5. An insecticidal, acaricidal or nematicidal agent, which contains an effective amount of a compound of the formula I or of the formula Ia in combination with suitable formulation auxiliaries.

6. A method of combating harmful insects, acarids or nematodes, which comprises applying an effective amount of a compound of the formula I or Ia as defined in claim 1 to these or to plants, areas or substrates infested by them.

7. A veterinary pharmaceutical, which contains a compound of the formula I or of the formula Ia as claimed in claim 1 or consists of this compound in combination with suitable formulation auxiliaries.

8. An agent for combating ecto- and endoparasites on animals, which contains a compound of the formula I or of the formula Ia as claimed in claim 1, in addition to suitable formulation auxiliaries.

9. A method of combating ecto- and endoparasites on animals, which comprises treating these with an agent as claimed in claim 8.

* * * * *

UNITED STATES PATENT AND TRADEMARK OFFICE
CERTIFICATE OF CORRECTION

PATENT NO. : 5,162,327
DATED : Nov. 10, 1992
INVENTOR(S) : Kratt et al.

It is certified that error appears in the above-identified patent and that said Letters Patent is hereby corrected as shown below:

Claim 1, column 27, line 21, please replace "holo($C_1$-$C_4$)-alkyl" with --halo($C_1$-$C_4$)-alkyl--;

Claim 3, column 29, line 5, after "M,D,E,", please delete "denote"; and

Claim 3, column 29, line 7, after "Q and G", please insert --denote--.

Signed and Sealed this

Ninth Day of November, 1993

Attest:

BRUCE LEHMAN

*Attesting Officer*     *Commissioner of Patents and Trademarks*